(12) United States Patent
Guzi et al.

(10) Patent No.: US 7,196,092 B2
(45) Date of Patent: Mar. 27, 2007

(54) N-HETEROARYL PYRAZOLOPYRIMIDINES AS CYCLIN DEPENDENT KINASE INHIBITORS

(75) Inventors: Timothy J. Guzi, Chatham, NJ (US); Kamil Paruch, Garwood, NJ (US); Michael P. Dwyer, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/244,776

(22) Filed: Oct. 6, 2005

(65) Prior Publication Data
US 2006/0040958 A1 Feb. 23, 2006

Related U.S. Application Data

(63) Continuation-in-part of application No. 10/654,157, filed on Sep. 3, 2003, now Pat. No. 7,078,525.

(60) Provisional application No. 60/408,030, filed on Sep. 4, 2002.

(51) Int. Cl.
- *A61K 31/519* (2006.01)
- *C07D 487/04* (2006.01)
- *A61P 37/00* (2006.01)
- *A61P 19/02* (2006.01)
- *A61P 29/00* (2006.01)

(52) U.S. Cl. .................................. 514/259.3; 544/281
(58) Field of Classification Search ........... 514/259.31, 514/259.3; 544/281
See application file for complete search history.

(56) References Cited

OTHER PUBLICATIONS

Bing, H.; S and G2 Phase Roles for Cdk2 Revealed by Inducible Expression of a Dominant-Negative Mutant in Human Cells; Mol. Cell. Biol.; 2001; 21(8); 2755-2766. Exhibit V, Iddb3 the database on investigational drugs (Jun. 1, 2205 update), Alvocidib.*
van del Heuvel, S.; Distinct Roles for Cyclin Dependent Kinases in Cell Cycle Control; Science; 1991; 262, 2050-2053. Exhibit VI, Iddb3 the database on investigational drugs (Jun. 1, 2005 update), Seliciclib. Fischer, P.M.; CDK inhibitors in clinical development for the treatment of cancer; Expert Opin. Investig. Drugs; 2003; 12(6); 955-970.*
Byrd, J.; Treatment of Relapsed Chronic Lymphocuic Leukemia by 72-Hour continuous Infusion orl-Hour Bolus Infusion of Flavopiridol: Results from Cancer and Leukemia Group B mudy19805; Clin. Cancer. Res.; 2005, 11(11), 4176-4181.*
Brwon, J.; Chronic Lymphocytic Leukemia: A Niche for Flavopiridol?;Clin. Cancer. Res.; 2005, 11(11), 3971-3973. Exhibit VII, Iddb3 the database on investigational drugs (Jun. 1, 2205 update), SNS-032.*

* cited by examiner

*Primary Examiner*—Mark L. Berch
*Assistant Examiner*—Susanna Moore
(74) *Attorney, Agent, or Firm*—Palaiyur S. Kalyanaraman

(57) ABSTRACT

In its many embodiments, the present invention provides a novel class of pyrazolo[1,5-a]pyrimidine compounds as inhibitors of cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions.

9 Claims, No Drawings

N-HETEROARYL PYRAZOLOPYRIMIDINES AS CYCLIN DEPENDENT KINASE INHIBITORS

REFERENCE TO PRIORITY APPLICATIONS

This application is a Continuation-in-Part of U.S. application Ser. No. 10/654,157 filed Sep. 3, 2003 issued as U.S. Pat. No. 7,078,525 (which published as U.S. 2004/0102451), which claims the benefit of priority from U.S. Provisional Patent Application Ser. No. 60/408,030, filed on Sep. 4, 2002.

FIELD OF THE INVENTION

The present invention relates to pyrazolo[1,5-a]pyrimidine compounds useful as protein kinase inhibitors, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

BACKGROUND OF THE INVENTION

The cyclin-dependent kinases (CDKs) are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, J. Clin. Oncol. (1998) 16, 2986–2999.

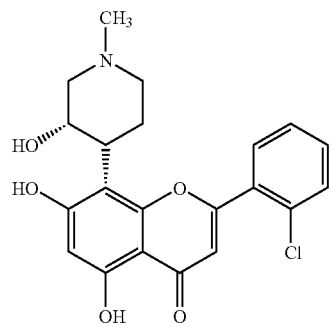

Formula I

Other known inhibitors of the CDKs include, for example, olomoucine (J. Vesely et al, Eur. J. Biochem., (1994) 224, 771–786) and roscovitine (I. Meijer et al, Eur. J. Biochem., (1997) 243, 527–536). U.S. Pat. No. 6,107,305 describes certain pyrazolo[3,4-b]pyridine compounds as CDK inhibitors. An illustrative compound from the '305 patent has the Formula II:

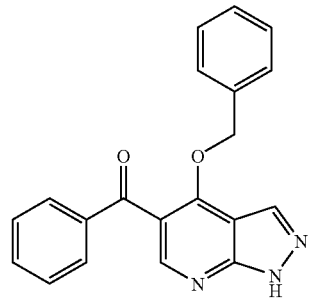

Formula II

K. S. Kim et al, J. Med. Chem. 45 (2002) 3905–3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383, 790, Chem. Pharm. Bull., (1999) 47 928, J. Med. Chem., (1977) 20, 296, J. Med. Chem., (1976) 19 517 and Chem. Pharm. Bull., (1962) 10 620 disclose various pyrazolopyrimidines.

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of pyrazolo[1,5-a]pyrimidine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts, solvates, esters or prodrugs of said compound, said compound having the general structure shown in Formula III:

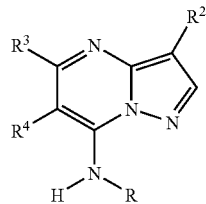

Formula III wherein:

R is heteroaryl, wherein said heteroaryl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^6$, —$C(R^4R^5)_nOR^5$, —$C(O_2)R^5$, —$C(O)R^5$, —$C(O)NR^5R^6$, —$SR^6$, —$S(O_2)R^7$, —$S(O_2)NR^5R^6$, —$N(R^5)S(O_2)R^7$, —$N(R^5)C(O)R^7$ and —$N(R^5)C(O)NR^5R^6$;

$R^2$ is selected from the group consisting of $R^9$, alkyl, alkynyl, aryl, heteroaryl, $CF_3$, heterocyclylalkyl, alkynylalkyl, cycloalkyl, —$C(O)OR^4$, alkyl substituted with 1-6 $R^9$ groups which can be the same or different and are independently selected from the list of $R^9$ shown later below,

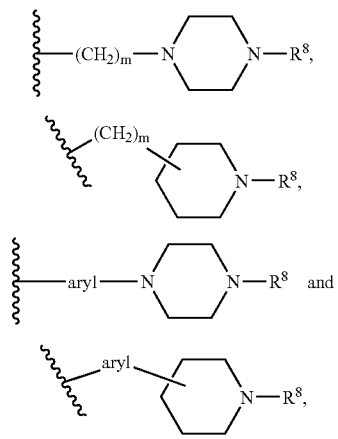

wherein the aryl in the above-noted definitions for $R^2$ can be unsubstituted or optionally substituted with one or more moieties which can be the same or different, each moiety being independently selected from the group consisting of halogen, CN, —$OR^5$, $SR^5$, —$CH_2OR^5$, —$C(O)R^5$, —$SO_3H$, —$S(O_2)R^6$, —$S(O_2)NR^5R^6$, —$NR^5R^6$, —$C(O)NR^5R^6$, —$CF_3$, and —$OCF_3$;

$R^3$ is selected from the group consisting of H, halogen, —$NR^5R^6$, —$C(O)OR^4$, —$C(O)NR^5R^6$, alkyl, alkynyl, cycloalkyl, cycloalkylalkyl, aryl, arylalkyl, heterocyclyl, heterocyclylalkyl, heteroaryl,

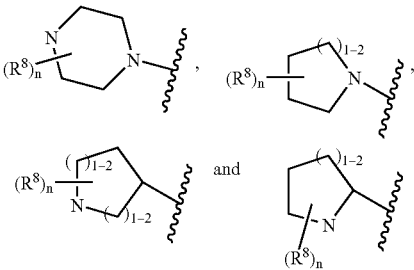

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, —$OCF_3$, —$(CR^4R^5)_nOR^5$, —$OR^5$, —$NR^5R^6$, —$(CR^4R^5)_nNR^5R^6$, —$C(O_2)R^5$, —$C(O)R^5$, —$C(O)NR^5R^6$, —$SR^6$, —$S(O_2)R^6$—$S(O_2)NR^5R^6$, —$N(R^5)S(O_2)R^7$, —$N(R^5)C(O)R^7$ and —$N(R^5)C(O)NR^5R^6$;

$R^4$ is H, halo or alkyl;

$R^5$ is H or alkyl;

$R^6$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$N(R^5)Boc$, —$(CR^4R^5)_nOR^5$, —$C(O_2)R^5$, —$C(O)R^5$, —$C(O)NR^5R^{11}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^4R^5$, —$N(R^5)Boc$, —$(CR^4R^5)_nOR^5$, —$C(O_2)R^5$, —$C(O)NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$;

or optionally (i) $R^5$ and $R^{10}$ in the moiety —$NR^5R^{10}$, or
(ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl for $R^7$ can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —NR⁵R¹⁰, —CH₂OR⁵, —C(O₂)R⁵, —C(O)NR⁵R¹⁰, —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of R⁶, —C(O)NR⁵R¹⁰, —CH₂OR⁴, —C(O)OR⁶, —C(O)R⁷ and —S(O₂)R⁷;

R⁹ is selected from the group consisting of halogen, —CN, —NR⁵R⁶, —(CH₂)ₙOR⁴, —C(O₂)R⁶, —C(O)NR⁵R⁶, —OR⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶;

m is 0 to 4; and n is 1 to 4.

In another embodiment, this invention discloses a compound of Formula IV:

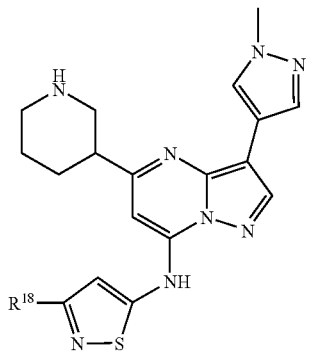

Formula IV wherein R¹⁸ is an alkyl or heterocyclyl with said heterocyclyl being linked to the isothiazole ring shown in the formula above via a carbon atom on said heterocyclyl, or a pharmaceutically acceptable salt, solvate, ester or prodrug of said compound.

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]pyrimidine compounds which are represented by structural Formula II, or a pharmaceutically acceptable salt, solvate, ester or prodrug thereof, wherein the various moieties are as described above.

In another embodiment, R is 2-pyridyl, 4-pyridyl, 3-pyridyl, 4-pyridyl-N-oxide, 3-pyridyl-N-oxide, 1,3-thiazol-2-yl, pyrimidin-5-yl, pyrazin-3-yl and pyridazin-3-yl wherein each of said pyridyl, thiazolyl, pyrimidinyl, pyrazinyl and pyridazinyl moieties can be unsubstituted or optionally independently substituted with one or more moieties which can be the same or different, each moiety being independently selected from the group consisting of halogen, alkyl, arylCF₃, OCF₃, CN, —OR⁵, —NR⁵R⁶, —CH₂OR⁵, —C(O₂)R⁵, —C(O)NR⁵R⁶, —S(O₂)NR⁵R⁶, and —N(R⁵)S(O₂)R⁷.

In another embodiment, R² is halogen, CF₃, CN, lower alkyl, cycloalkyl, —OR⁶, —C(O)OR⁴, —CH₂OR⁶, aryl or heteroaryl.

In another embodiment, R³ is H, halogen, lower alkyl, aryl, heteroaryl, —C(O)OR⁴, cycloalkyl, —NR⁵R⁶, heterocyclylalkyl, cycloalkylalkyl,

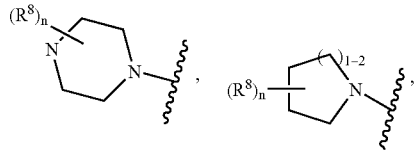

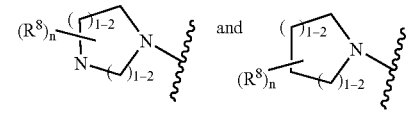

wherein said alkyl, aryl, heteroaryl, heterocyclyl and cycloalkyl for R³ are unsubstituted or optionally independently substituted with one or more moieties which can be the same or different, each moiety being independently selected from the group consisting of halogen, CF₃, OCF₃, lower alkyl, CN and OR⁵.

In another embodiment, R⁴ is H, halo, or lower alkyl.

In another embodiment, R⁵ is H or lower alkyl.

In another embodiment, m is 0 to 2.

In another embodiment, n is 1 to 2.

In an additional embodiment, R is 2-pyridyl, 4-pyridyl, 3-pyridyl, 4-pyridyl-N-oxide, 3-pyridyl-N-oxide, 1,3-thiazol-2-yl, pyrimidin-5-yl, pyrazin-3-yl and pyridazin-3-yl.

In an additional embodiment, R² is F, Cl, Br, CF₃, CN, lower alkyl, cycloalkyl or —(CH₂)ₙOR⁶.

In an additional embodiment, R³ is H, lower alkyl, cycloalkyl, —C(O)OR⁴, aryl, heteroaryl, cycloalkylalkyl,

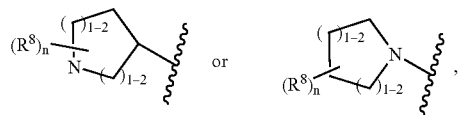

wherein each of said lower alkyl, cycloalkyl, heteroaryl and aryl are unsubstituted or optionally independently substituted with one or more moieties which can be the same or different, each moiety being independently selected from the group consisting of halogen, CF₃, lower alkyl, OMe and CN.

In an additional embodiment, R³ is:

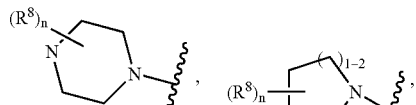

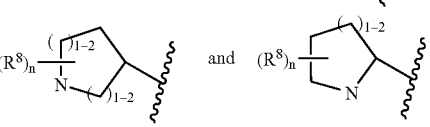

In a still additional embodiment, R³ is

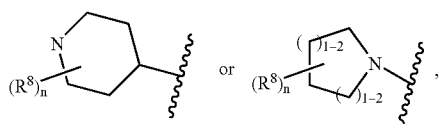

In an additional embodiment, R⁴ is H.
In an additional embodiment, R⁵ is H.
In an additional embodiment, m is 0.
In an additional embodiment, n is 1.
In another embodiment of Formula IV, R¹⁸ is methyl.

In an additional embodiment of Formula IV, R¹⁸ is a heterocyclyl with said heterocyclyl being selected from the group consisting of:

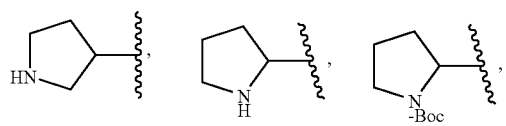

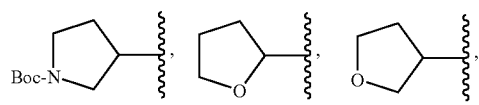

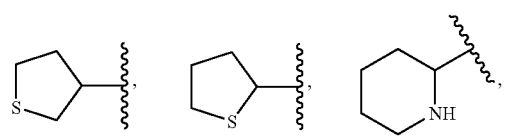

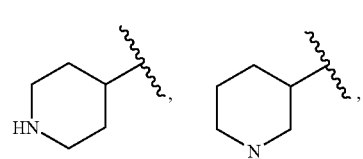

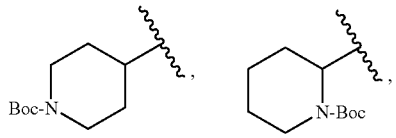

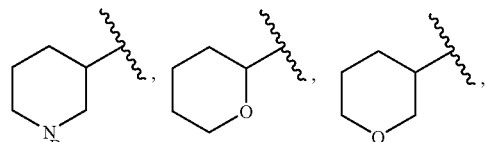

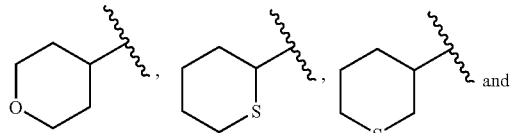 and

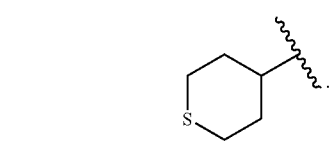

In an additional embodiment of Formula IV, R¹⁸ is a heterocyclyl shown below:

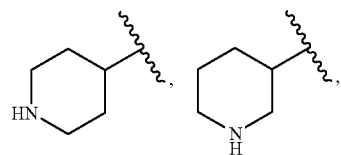

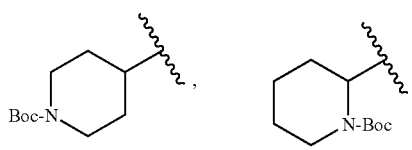

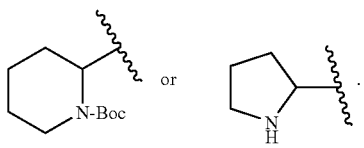 or

In an additional embodiment, this invention discloses a compound of formula:

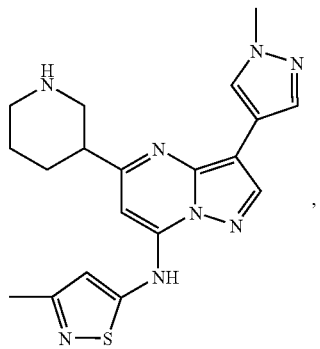

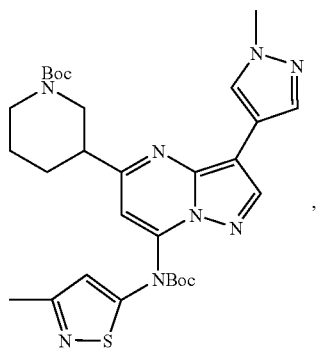

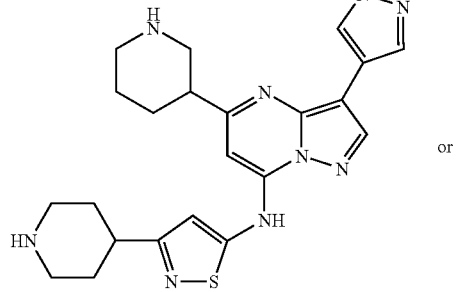 or

-continued
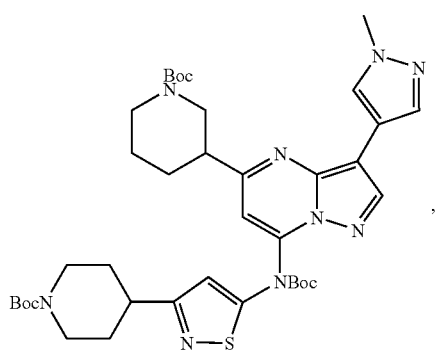
or a pharmaceutically acceptable salt, solvate, ester or prodrug of said compound.
An inventive group of compounds are shown in Table 1.
TABLE 1
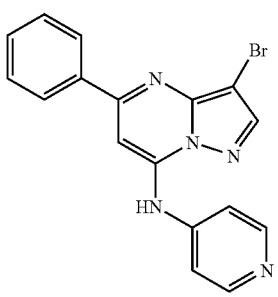
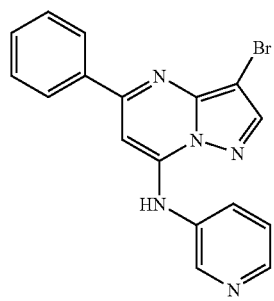
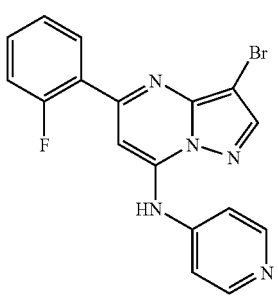
TABLE 1-continued
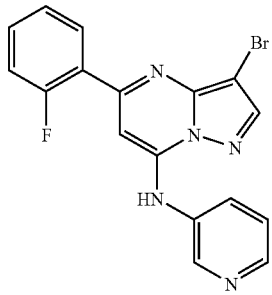
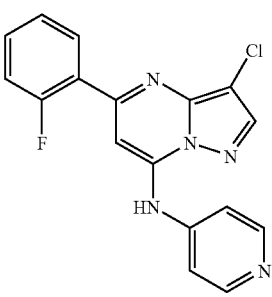
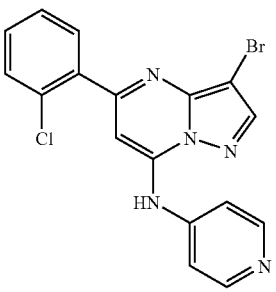
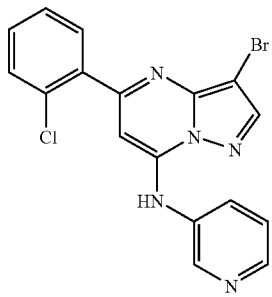

TABLE 1-continued
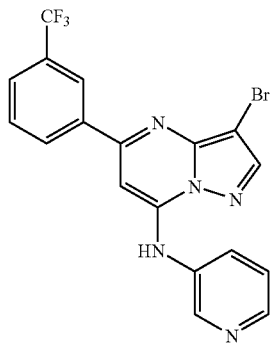
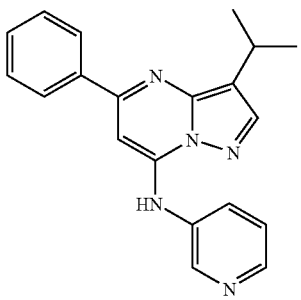
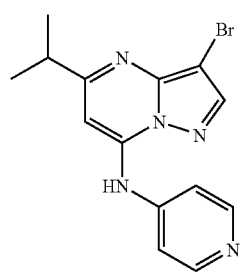
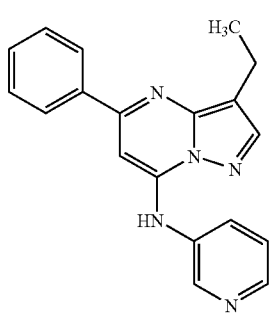
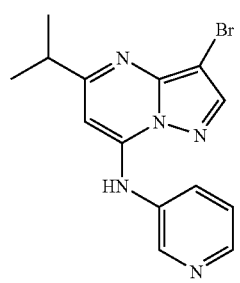
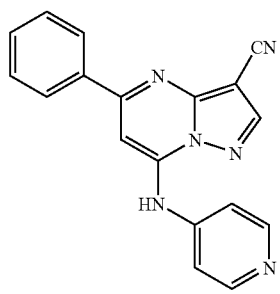
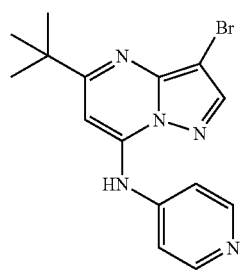
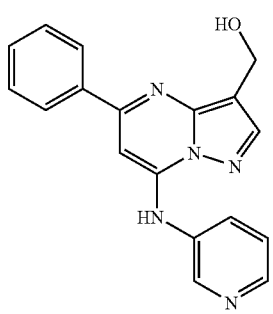
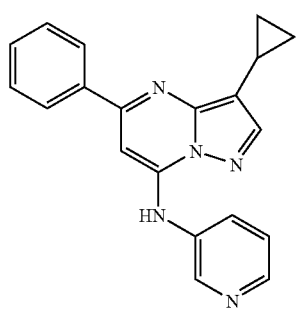
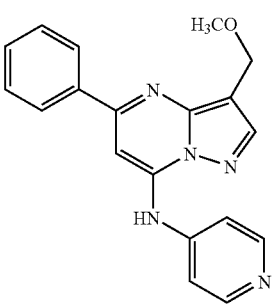

TABLE 1-continued
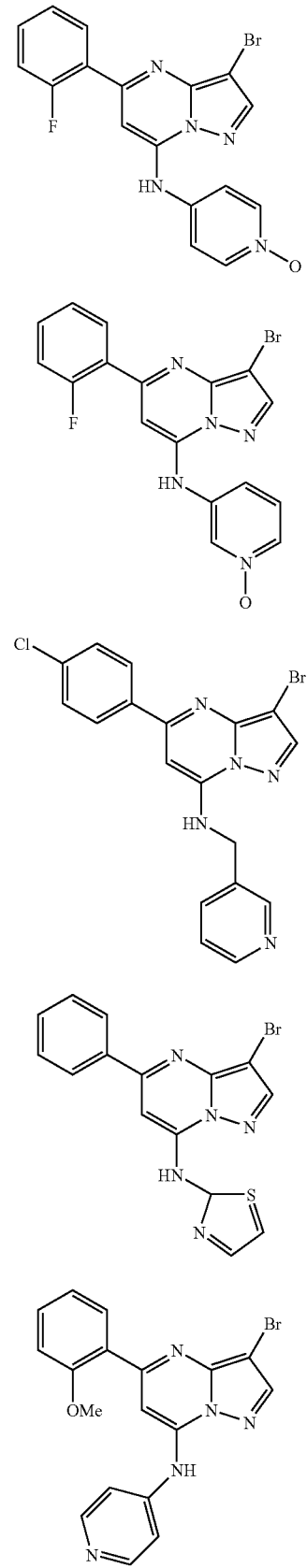
TABLE 1-continued
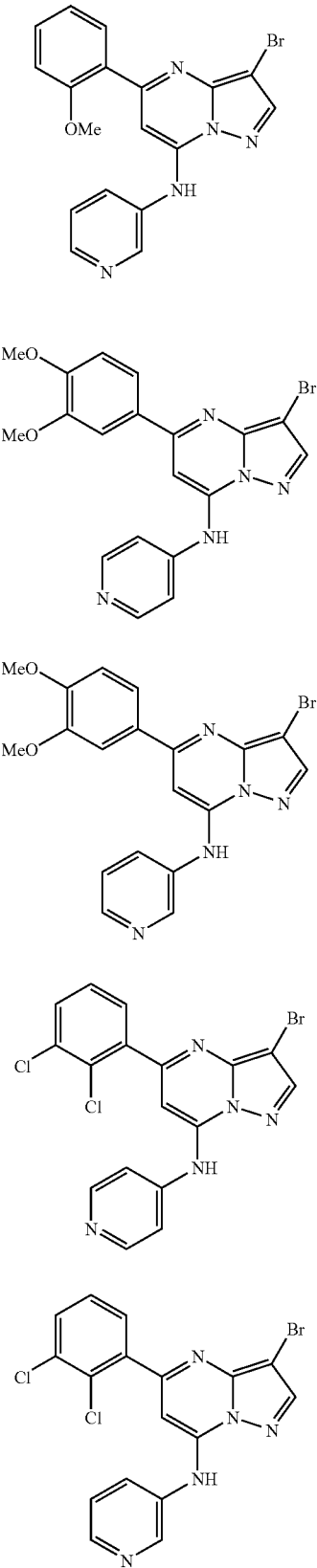

TABLE 1-continued
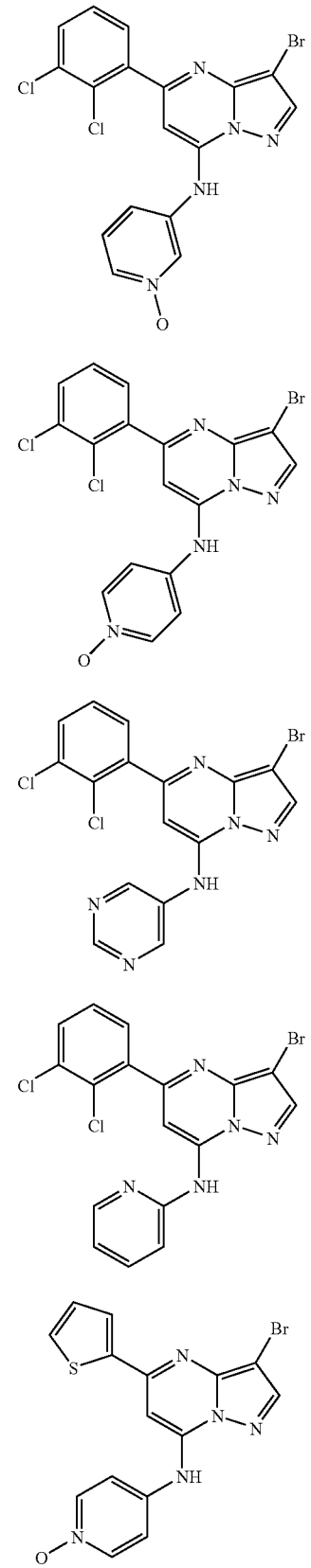
TABLE 1-continued
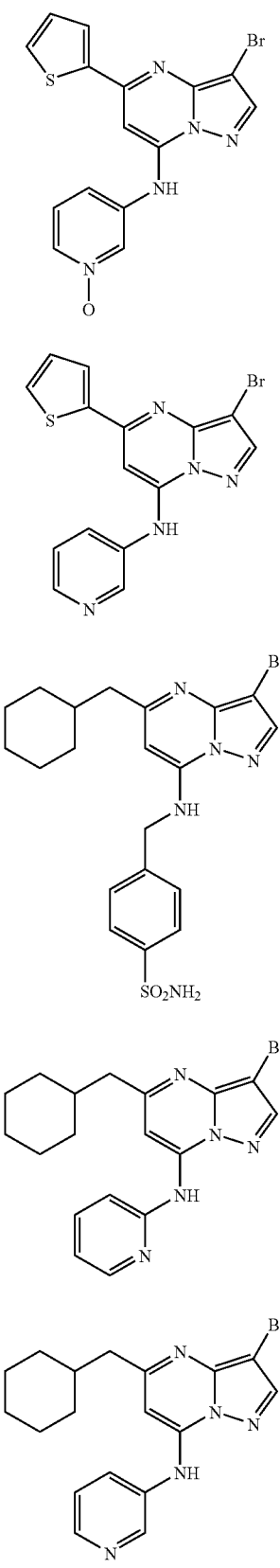

TABLE 1-continued
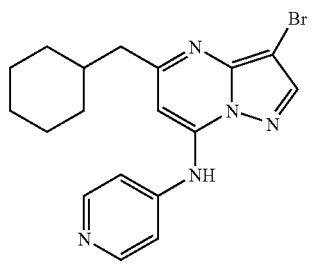
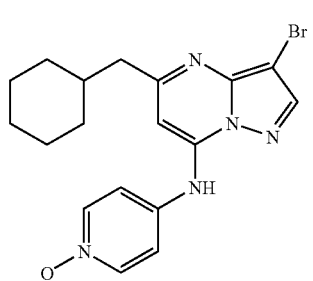
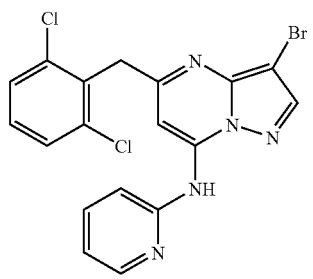
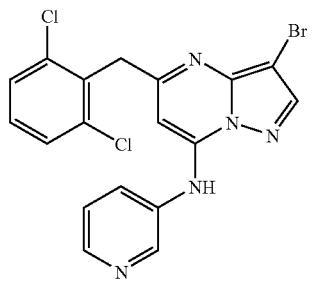
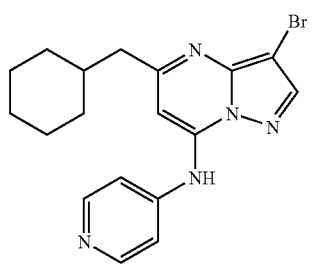
TABLE 1-continued
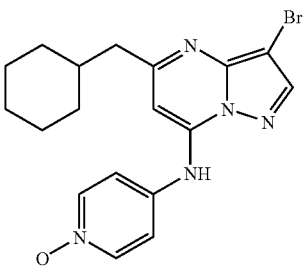
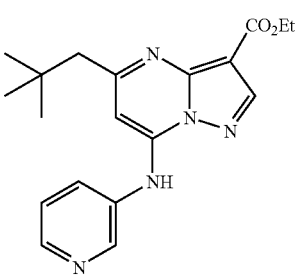
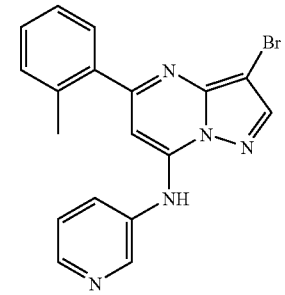
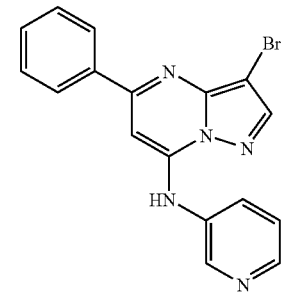
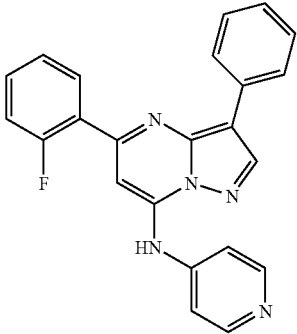

TABLE 1-continued
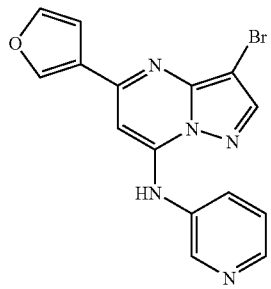
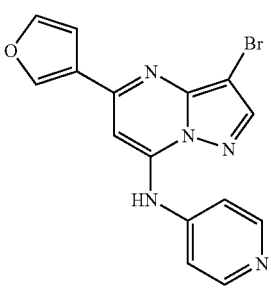
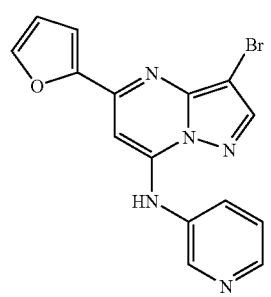
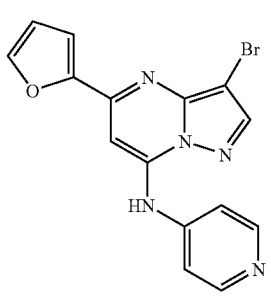
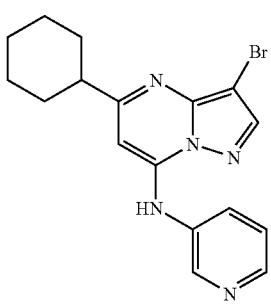
TABLE 1-continued
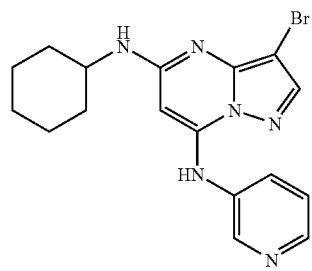
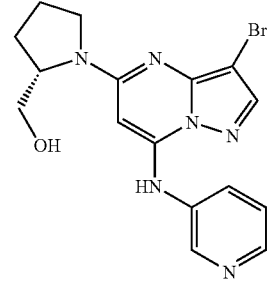
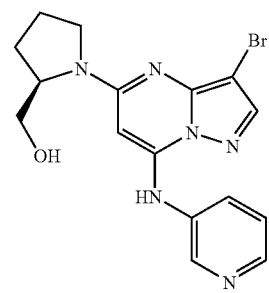
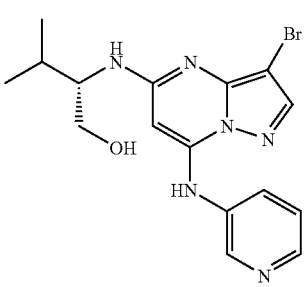
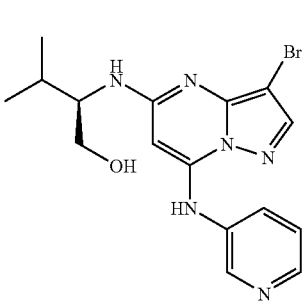

TABLE 1-continued
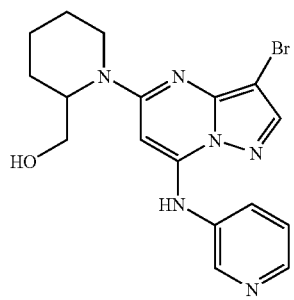
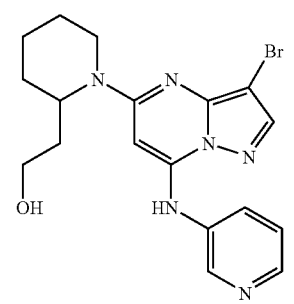
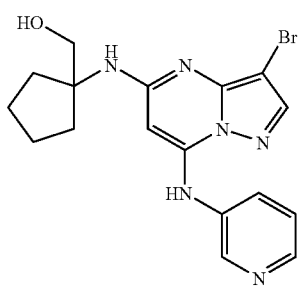
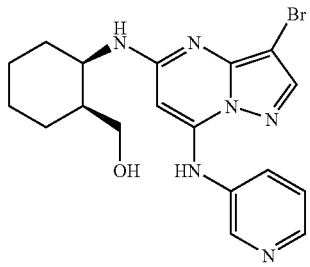
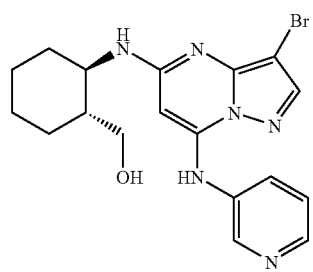
TABLE 1-continued
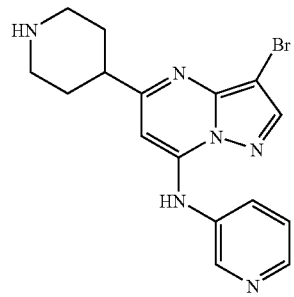
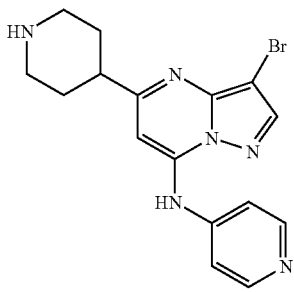
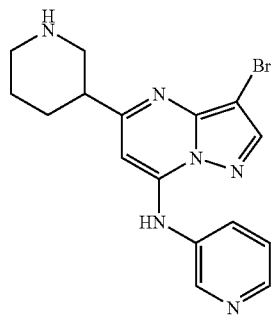
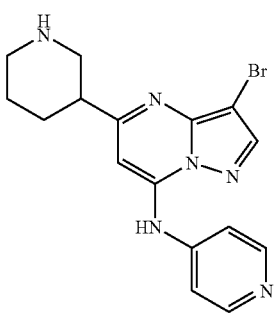
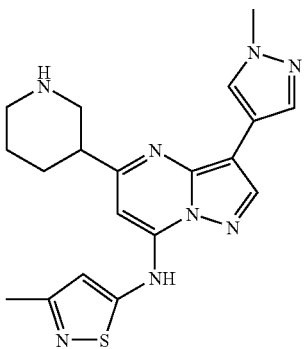

TABLE 1-continued

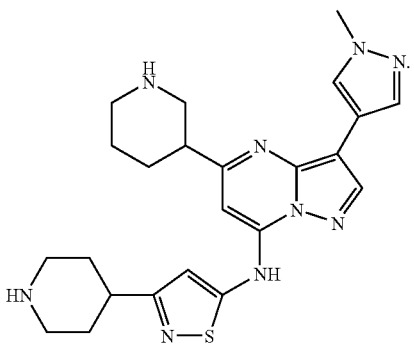

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

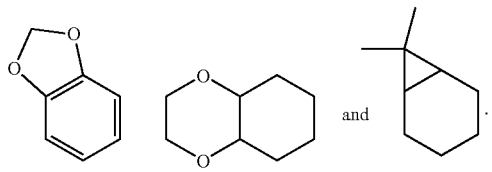

and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

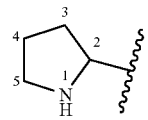

there is no —OH attached directly to carbons marked 2 and 5.

It should also be noted that tautomeric forms such as, for example, the moieties:

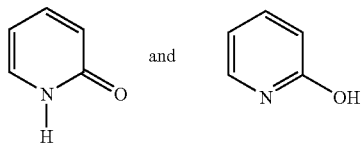

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987)

Edward B. Roche, ed., American Pharmaceutical Association and Pergamon Press. The term "prodrug" means a compound (e.g, a drug precursor) that is transformed in vivo to yield a compound of Formula (III) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (III) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1–C_8)$alkyl, $(C_2–C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1–C_2)$alkylamino$(C_2–C_3)$alkyl (such as β-dimethylaminoethyl), carbamoyl-$(C_1–C_2)$alkyl, N,N-di $(C_1–C_2)$alkylcarbamoyl-(C1–C2)alkyl and piperidino-, pyrrolidino- or morpholino$(C_2–C_3)$alkyl, and the like.

Similarly, if a compound of Formula (III) contains an alcohol functional group, a prodrug can be formed by the replacement of the hydrogen atom of the alcohol group with a group such as, for example, $(C_1–C_6)$alkanoyloxymethyl, 1-($(C_1–C_6)$alkanoyloxy)ethyl, 1-methyl-1-($(C_1–C_6)$alkanoyloxy)ethyl, $(C_1–C_6)$alkoxycarbonyloxymethyl, N-$(C_1–C_6)$alkoxycarbonylaminomethyl, succinoyl, $(C_1–C_6)$ alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1–C_6)$alkyl$)_2$ or glycosyl (the radical resulting from the removal of a hydroxyl group of the hemiacetal form of a carbohydrate), and the like.

If a compound of Formula (III) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1–C_{10})$ alkyl, $(C_3–C_7)$ cycloalkyl, benzyl, or R-carbonyl is a natural α-aminoacyl or natural α-aminoacyl, —$C(OH)C(O)OY^1$ wherein $Y^1$ is H, $(C_1–C_6)$alkyl or benzyl, —$C(OY^2)Y^3$ wherein $Y^2$ is $(C_1–C_4)$ alkyl and $Y^3$ is $(C_1–C_6)$alkyl, carboxy $(C_1–C_6)$alkyl, amino$(C_1–C_4)$alkyl or mono-N- or di-N,N-$(C_1–C_6)$alkylaminoalkyl, —$C(Y^4)Y^5$ wherein $Y^4$ is H or methyl and $Y^5$ is mono-N- or di-N,N-$(C_1–C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601–611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603–604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formulas III and IV can form salts which are also within the scope of this invention. Reference to a compound of Formulas III and IV herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III or IV contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III or IV may be formed, for example, by reacting a compound of Formula III or IV with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$) acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (III) may contain asymmetric or chiral centers, and, therefore, exist in different stereoisomeric forms. It is intended that all stereoisomeric forms of the compounds of Formula (III) as well as mixtures thereof, including racemic mixtures, form part of the present invention. In addition, the present invention embraces all geometric and positional isomers. For example, if a compound of Formula (III) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (III) may be atropisomers (e.g., substituted biaryls) and are considered as part of this invention. Enantiomers can also be separated by use of chiral HPLC column.

It is also possible that the compounds of Formula (III) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (III) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (III) may be atropisomers (e.g., substituted biaryls) and are considered as part of this invention. Enantiomers can also be separated, for example, by use of chiral HPLC column.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (III) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (III) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula III or IV, and of the salts, solvates, esters and prodrugs of the compounds of Formula III or IV, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds according to the invention have pharmacological properties; in particular, the compounds of Formulas III and IV can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 CDK8 and CDK9. The novel compounds of Formulas III and IV are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formulas III and IV can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulas III and IV may also be useful in the treatment of Alzheimer's disease, as suggested by the recent finding that CDK5 is involved in the phosphorylation of tau protein (J. Biochem, (1995) 117, 741–749).

Compounds of Formulas III and IV may induce or inhibit apoptosis. The apoptotic response is aberrant in a variety of human diseases. Compounds of Formula III or IV, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula III and IV, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III and IV may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III and IV may also be useful in inhibiting tumor angiogenesis and metastasis.

Compounds of Formula III and IV may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III or IV, or a pharmaceutically acceptable salt or solvate of said compound to the mammal.

A preferred dosage is about 0.001 to 500 mg/kg of body weight/day of the compound of Formula III or IV. An especially preferred dosage is about 0.01 to 25 mg/kg of body weight/day of a compound of Formula III or IV, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (gefitinib, from Astra Zeneca Pharmaceuticals, England), Tarceva® (erlotinib hydrochloride, EGFR kinase inhibitors), antibodies to EGFR (e.g., C225), Gleevec® (imatinib C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux® (cetuximab) Liposomal, Thiotepa, Altretamine, Melphalan, Trastuzumab, Lerozole, Fulvestrant, Exemestane, Fulvestrant, Ifosfomide, Rituximab, C225 (or Cetuximab from Merck KGaA, Darmstadt, Germany), and Campath.

The compounds of this invention may specifically be useful in combination (administered together, concurrently or sequentially) with temozolomide and/or radiation therapy.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III and IV may also be administered sequentially with known anticancer or cytotoxic agents when a combination formulation is inappropriate. The invention is not limited in the sequence of administration; compounds of Formula III and IV may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula III or IV, or a pharmaceutically acceptable salt, solvate, ester or prodrug thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula III or IV, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III or IV, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula III or IV, or a pharmaceutically acceptable salt, solvate, ester or prodrug of said compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given.

The following solvents and reagents may be referred to by their abbreviations in parenthesis:
Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.

EXAMPLES

In general, the compounds of the present invention can be prepared through the general routes described below in Scheme 1. Treatment of the

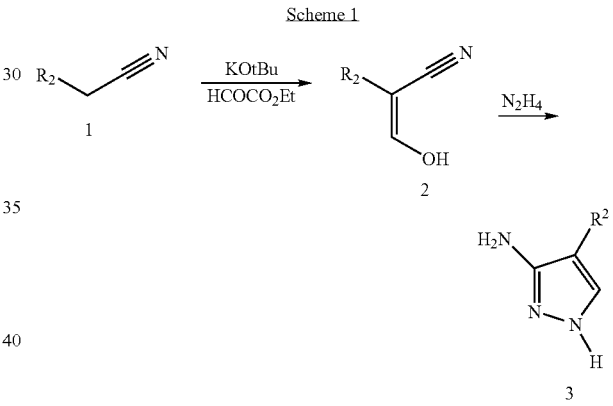

starting nitrile with potassium t-butoxide and ethyl formate gives rise to the intermediate enol 2 which upon treatment with hydrazine gives the desired substituted 3-aminopyrazole. Condensation of the compounds of type 3 with the appropriately functionalized keto ester of type 5 gives rise to the pyridones 6 as shown in Scheme 3. The keto esters used in this general route are either commercially available or can be made as illustrated in Scheme 2.

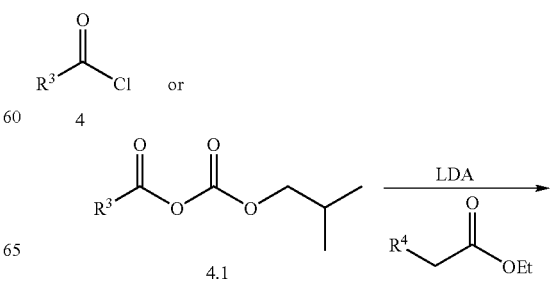

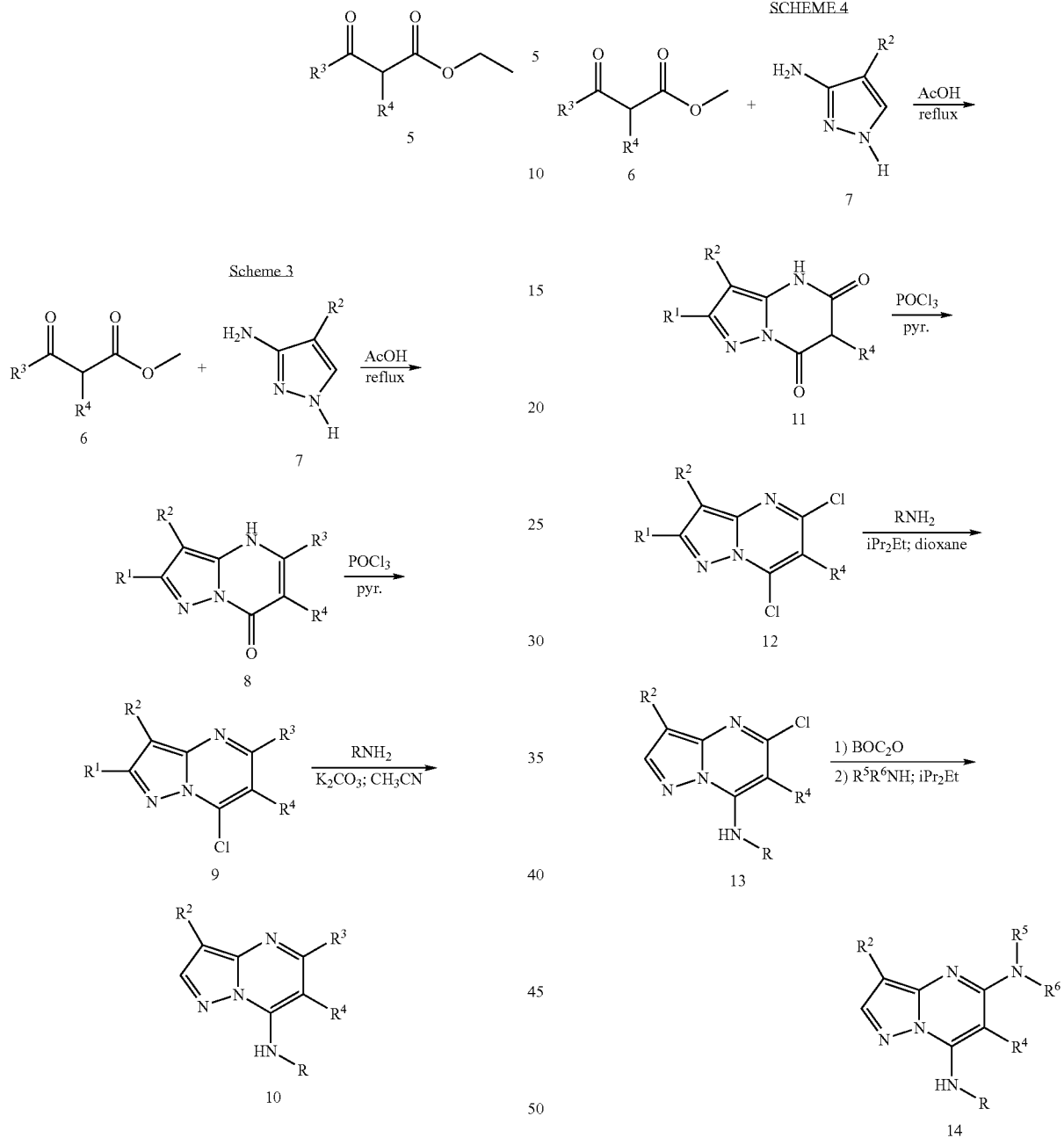

The chlorides of type 9 can be prepared by treatment of the pyridones 8 with $POCl_3$. When $R^2$ is equal to H, substitution in this position is possible on the compounds of type 9 by electrophilic halogenation, acylation, and various other electrophilic aromatic substitutions.

Introduction of the N7-amino functionality can be accomplished through displacement of the chloride of compounds of type 9 by reaction with the appropriate amine as shown in Scheme 3.

When $R^3$=OEt in compounds of type 6, the dichlorides of type 12 can easily be prepared as outlined in Scheme 4. Selective displacements of the 7-chloride gives rise to compounds of type 13, which can readily be converted to products of type 14.

PREPARATIVE EXAMPLES

Preparative Example 1

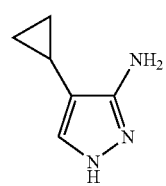

Step A:

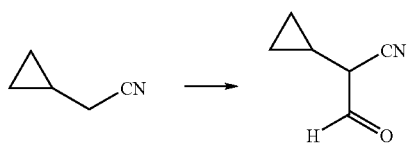

A procedure in German patent DE 19834047 A1, p 19 was followed. To a solution of KOtBu (6.17 g, 0.055 mol) in anhydrous THF (40 mL) was added, dropwise, a solution of cyclopropylacetonitrile (2.0 g, 0.025 mol) and ethyl formate (4.07 g, 0.055 mol) in anhydrous THF (4 mL). A precipitate formed immediately. This mixture was stirred for 12 hr. It was concentrated under vacuum and the residue stirred with $Et_2O$ (50 mL). The resulting residue was decanted and washed with $Et_2O$ (2×50 mL) and $Et_2O$ removed from the residue under vacuum. The residue was dissolved in cold $H_2O$ (20 mL) and pH adjusted to 4–5 with 12 N HCl. The mixture was extracted with $CH_2Cl_2$ (2×50 mL). The organic layers were combined, dried over $MgSO_4$ and concentrated under vacuum to give the aldehyde as a tan liquid.

Step B:

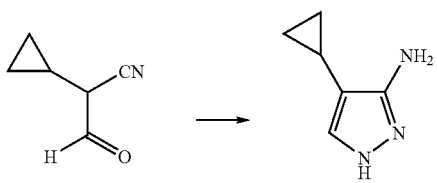

The product from Preparative Example 1, Step A (2.12 g, 0.0195 mol), $NH_2NH_2H_2O$ (1.95 g, 0.039 mol) and 1.8 g (0.029 mole) of glacial $CH_3CO_2H$ (1.8 g, 0.029 mol) were dissolved in EtOH (10 mL). It was refluxed for 6 hr and concentrated under vacuum. The residue was slurried in $CH_2Cl_2$ (150 mL) and the pH adjusted to 9 with 1N NaOH. The organic layer was washed with brine, dried over $MgSO_4$ and concentrated under vacuum to give the product as a waxy orange solid.

Preparative Examples 2–4

By essentially the same procedure set forth in Preparative Example 1, only substituting the nitrile shown in Column 2 of Table 2, the compounds in Column 3 of Table 2 were prepared:

TABLE 2

| Prep. Ex. | Column 2 | Column 3 |
|---|---|---|
| 2 | | |
| 3 | $H_3C\!-\!\!\diagup\!\!\diagdown\!\!-CN$ $H_3C$ | $H_3C\!-\!\diagdown$ pyrazole-$NH_2$ |

Preparative Example 4

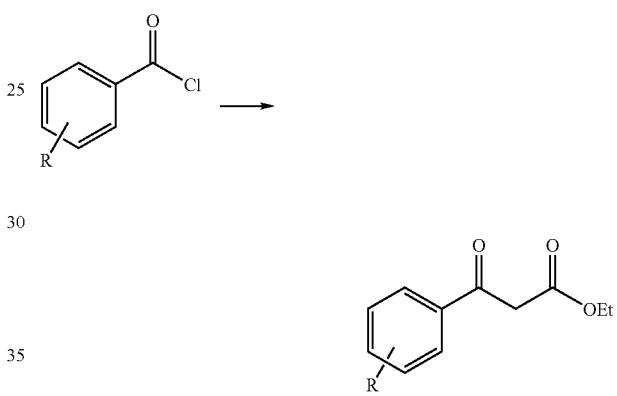

The reactions were done as outlined in (K. O. Olsen, *J. Org. Chem.*, (1987) 52, 4531–4536). Thus, to a stirred solution of lithium diisopropylamide in THF at −65 to −70° C. was added freshly distilled ethyl acetate, dropwise. The resulting solution was stirred for 30 min and the acid chloride was added as a solution in THF. The reaction mixture was stirred at −65 to −70° C. for 30 min and then terminated by the addition of 1 N HCl solution. The resulting two-phased mixture was allowed to warm to ambient temperature. The resulting mixture was diluted with EtOAc (100 mL) the organic layer was collected. The aqueous layer was extracted with EtOAc (100 mL). The organic layers were combined, washed with brine, dried ($Na_2SO_4$), and concentrated in vacuo to give the crude β-keto esters, which were used in the subsequent condensations.

Preparative Examples 5–10

By essentially the same procedure set forth in Preparative Example 4 only substituting the acid chlorides shown in Column 2 of Table 3, the β-keto esters shown in Column 3 of Table 3 were prepared:

TABLE 3

| Prep. Ex. | Column 2 | Column 3 | DATA |
|---|---|---|---|
| 5 | 2-methoxybenzoyl chloride | ethyl 3-(2-methoxyphenyl)-3-oxopropanoate | Yield = 99%<br>LCMS: MH$^+$ = 223 |
| 6 | 3,4-dimethoxybenzoyl chloride | ethyl 3-(3,4-dimethoxyphenyl)-3-oxopropanoate | Yield = 99%<br>LCMS: MH$^+$ = 253 |
| 7 | 2,3-dichlorobenzoyl chloride | ethyl 3-(2,3-dichlorophenyl)-3-oxopropanoate | Yield = 80%<br>LCMS: MH$^+$ = 261 |
| 8 | thiophene-2-carbonyl chloride | ethyl 3-oxo-3-(thiophen-2-yl)propanoate | Yield = 93%<br>MH$^+$ = 199 |
| 9 | 3,3-dimethylbutanoyl chloride | ethyl 5,5-dimethyl-3-oxohexanoate | Yield = 93% |
| 10 | 2-methylbenzoyl chloride | ethyl 3-(2-methylphenyl)-3-oxopropanoate | Yield = 100% |

Preparative Example 11

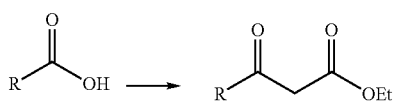

To a solution of the acid in THF was added Et$_3$N, followed by isobutyl chloroformate at −20 to −30° C. After the mixture was stirred for 30 min at −20 to −30° C., triethylamine hydrochloride was filtered off under argon, and the filtrate was added to the LDA-EtOAc reaction mixture (prepared as outlined in Method A) at −65 to −70° C. After addition of 1 N HCl, followed by routine workup of the reaction mixture and evaporation of the solvents, the crude β-keto esters were isolated. The crude material was used in the subsequent condensations.

Preparative Examples 12–13.12

By essentially the same conditions set forth in Preparative Example 11 only substituting the carboxylic acid shown in Column 2 of Table 4, the compounds shown in Column 3 of Table 4 were prepared:

TABLE 4

| Prep. Ex. | Column 2 | Column 3 | DATA |
| --- | --- | --- | --- |
| 12 | cyclohexyl-CH2-COOH | cyclohexyl-CH2-C(O)-CH2-C(O)OEt | Yield = 99%<br>MH+ = 213 |
| 13 | 2,6-dichlorophenyl-CH2-COOH | 2,6-dichlorophenyl-CH2-C(O)-CH2-C(O)OEt | Yield = 70%<br>MH+ = 275 |
| 13.10 | cyclohexyl-C(O)Cl | cyclohexyl-C(O)-CH2-C(O)OEt | Yield = 99<br>MH+ = 199 |
| 13.11 | CbzN-piperidin-4-yl-C(O)Cl | CbzN-piperidin-4-yl-C(O)-CH2-C(O)OEt | Yield = 99<br>MH+ = 334 |
| 13.12 | CbzN-piperidin-3-yl-C(O)Cl | CbzN-piperidin-3-yl-C(O)-CH2-C(O)OEt | Yield = 99<br>MH+ = 334 |

Preparative Example 13.13

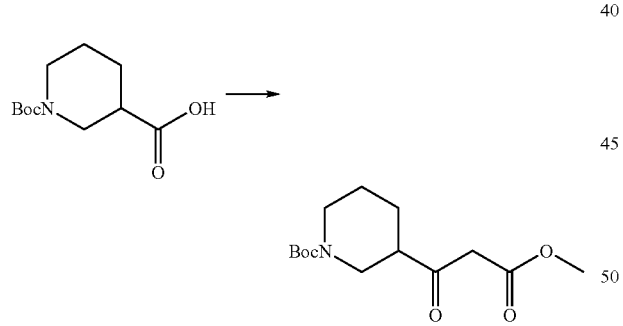

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (60 mL). The mixture was stirred at 25° C. for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, flitered, and the solvent was evaporated. The residue was dissolved in MeOH (580 mL), and the mixture was refluxed for 4 hr. The solvent was evaporated and the residue was purified by column chromatography on silicagel with 10:1 CH$_2$Cl$_2$/EtOAc as eluent. Pale yellow oil (26.5 g, 43%) was obtained.

Preparative Example 14

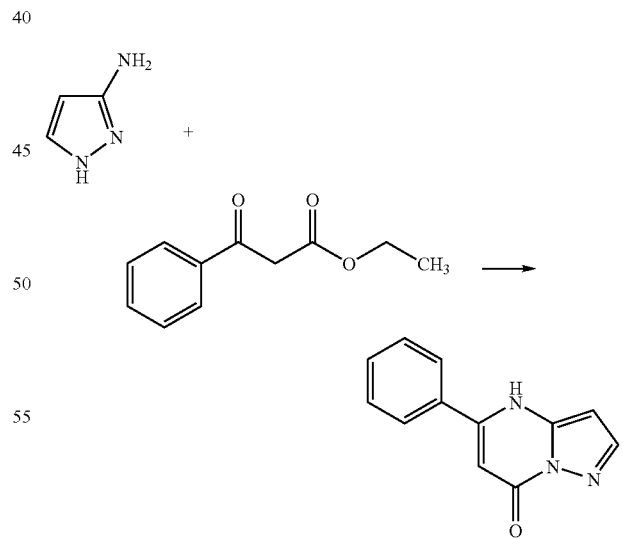

A solution of 3-aminopyrazole (2.0 g, 24.07 mmol) and ethyl benzoylacetate (4.58 mL, 1.1 eq.) in AcOH (15 mL) was heated at reflux for 3 hours. The reaction mixture was cooled to room temperature and concentrated in vacuo. The resulting solid was diluted with EtOAc and filtered to give a white solid (2.04 g, 40% yield).

Preparative Examples 15–32.16
By essentially the same procedure set forth in Preparative Example 14 only substituting the aminopyrazole shown in Column 2 of Table 5 and the ester shown in Column 3 of Table 5, the compounds shown in Column 4 of Table 5 were prepared:
TABLE 5
| Prep. Ex. | Column 2 | Column 3 | Column 4 |
|---|---|---|---|
| 15 | 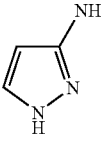 | 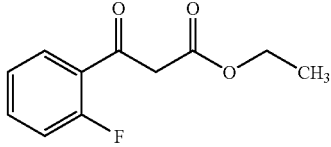 | 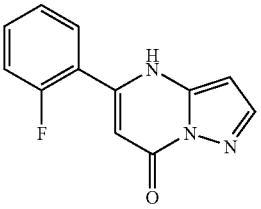 |
| 16 | 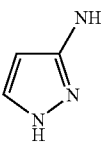 | 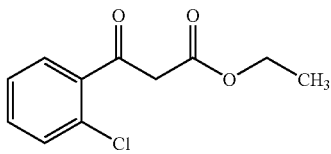 | 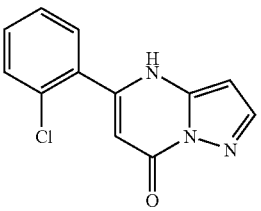 |
| 17 | 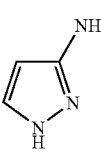 | 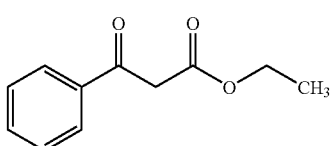 | 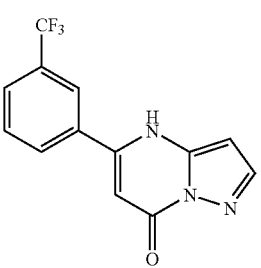 |
| 18 | 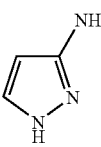 | 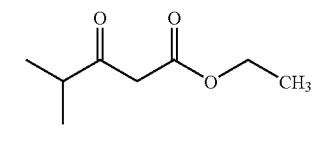 | 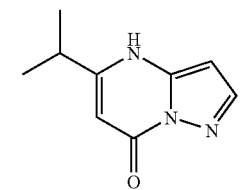 |
| 19 | 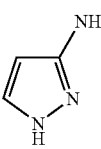 | 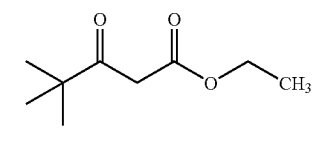 | 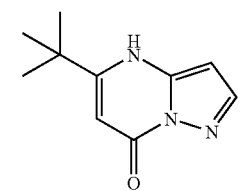 |
| 20 | 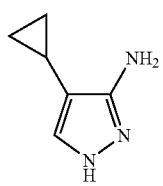 | 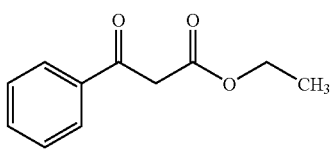 | 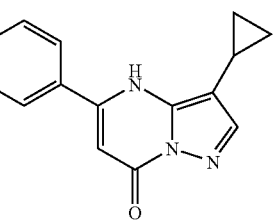 |

TABLE 5-continued

| Prep. Ex. | Column 2 | Column 3 | Column 4 |
|---|---|---|---|
| 21 | 4-isopropyl-1H-pyrazol-3-amine | ethyl 3-oxo-3-phenylpropanoate | 3-isopropyl-5-phenyl-4H-pyrazolo[1,5-a]pyrimidin-7-one |
| 22 | 4-ethyl-1H-pyrazol-3-amine | ethyl 3-oxo-3-phenylpropanoate | 3-ethyl-5-phenyl-4H-pyrazolo[1,5-a]pyrimidin-7-one |
| 23 | 1H-pyrazol-3-amine | methyl 3-(4-chlorophenyl)-3-oxopropanoate | 5-(4-chlorophenyl)-4H-pyrazolo[1,5-a]pyrimidin-7-one |
| 24 | 1H-pyrazol-3-amine | ethyl 3-(2-methoxyphenyl)-3-oxopropanoate | 5-(2-methoxyphenyl)-4H-pyrazolo[1,5-a]pyrimidin-7-one |
| 25 | 1H-pyrazol-3-amine | ethyl 3-(3,4-dimethoxyphenyl)-3-oxopropanoate | 5-(3,4-dimethoxyphenyl)-4H-pyrazolo[1,5-a]pyrimidin-7-one |
| 26 | 1H-pyrazol-3-amine | ethyl 3-(2,3-dichlorophenyl)-3-oxopropanoate | 5-(2,3-dichlorophenyl)-4H-pyrazolo[1,5-a]pyrimidin-7-one |
| 27 | 1H-pyrazol-3-amine | ethyl 3-oxo-3-(thiophen-2-yl)propanoate | 5-(thiophen-2-yl)-4H-pyrazolo[1,5-a]pyrimidin-7-one |

TABLE 5-continued
| Prep. Ex. | Column 2 | Column 3 | Column 4 |
|---|---|---|---|
| 28 | 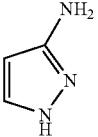 | 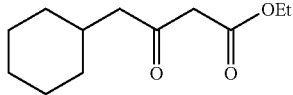 | 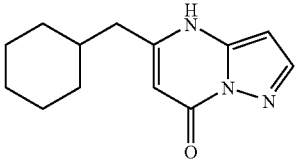 |
| 29 | 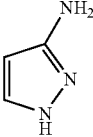 | 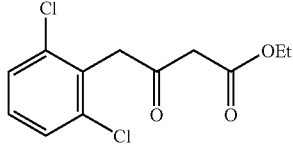 | 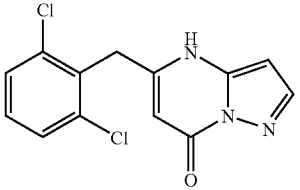 |
| 30 | 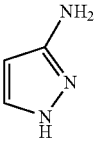 | 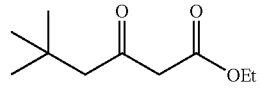 | 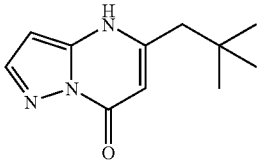 |
| 31 | 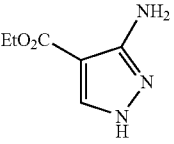 | 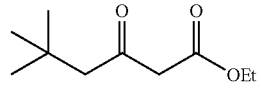 | 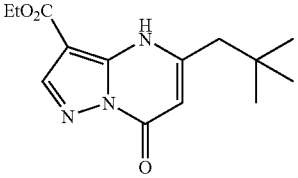 |
| 32 | 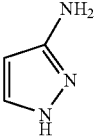 | 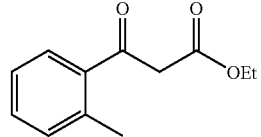 | 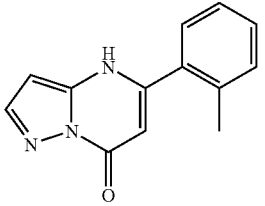 |
| 32.11 | 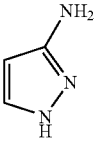 | 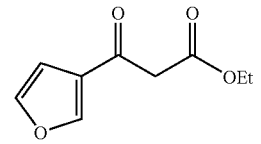 | 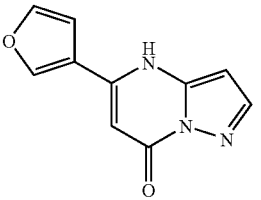 |
| 32.12 | 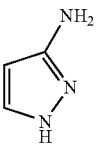 | 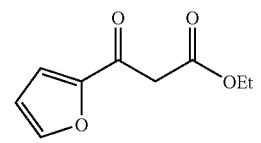 | 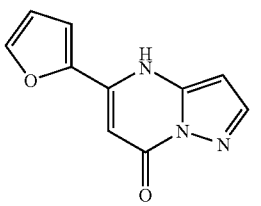 |

TABLE 5-continued
| Prep. Ex. | Column 2 | Column 3 | Column 4 |
|---|---|---|---|
| 32.13 | 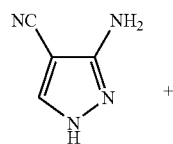 | | |
| 32.14 | | | |
| 32.15 | | | |
| 32.16 | | | |
Preparative Example 33
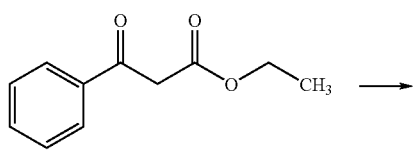
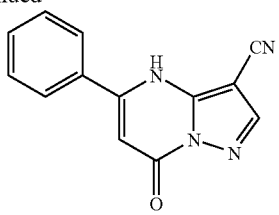
Ethyl benzoylacetate (1.76 mL, 1.1 eq.) and 3-amino-4-cyanopyrazole (1.0 g, 9.25 mmol) in AcOH (5.0 mL) and H$_2$O (10 mL) was heated at reflux 72 hours. The resulting solution was cooled to room temperature, concentrated in vacuo, and diluted with EtOAc. The resulting precipitate was filtered, washed with EtOAc, and dried in vacuo (0.47 g, 21% yield).

Preparative Example 33.10

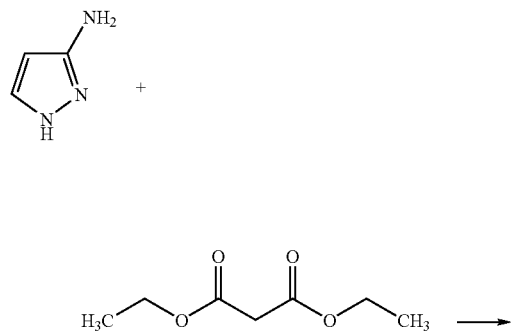

A procedure in U.S. Pat. No. 3,907,799 was followed. Sodium (2.3 g, 2 eq.) was added to EtOH (150 mL) portionwise. When the sodium was completely dissolved, 3-aminopyrazole (4.2 g, 0.05 mol) and diethyl malonate (8.7 g, 1.1 eq.) were added and the resulting solution heated to reflux for 3 hours. The resulting suspension was cooled to room temperature and filtered. The filter cake was washed with EtOH (100 mL) and dissolved in water (250 mL). The resulting solution was cooled in an ice bath and the pH adjusted to 1–2 with concentrated HCl. The resulting suspension was filtered, washed with water (100 mL) and dried under vacuum to give a white solid (4.75 g, 63% yield).

Preparative Examples 33.11–33.12

By essentially the same procedure set forth in Preparative Example 33.10 only substituting the compound shown in Column 2 of Table 5.1, the compounds shown in Column 3 of Table 5.1 are prepared:

TABLE 5.1

| Prep. Ex. | Column 2 | Column 3 |
|---|---|---|
| 33.11 | | |
| 33.12 | | |

Preparative Example 34

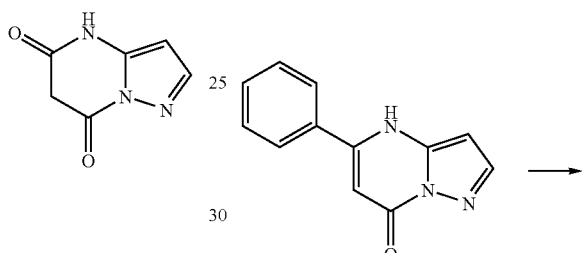

A solution of the compound prepared in Preparative Example 14 (1.0 g, 4.73 mmol) in POCl$_3$ (5 mL) and pyridine (0.25 mL) was stirred at room temperature 3 days. The resulting slurry was diluted with Et$_2$O, filtered, and the solid residue washed with Et$_2$O. The combined Et$_2$O washings were cooled to 0° C. and treated with ice. When the vigorous reaction ceased, the resulting mixture was diluted with H$_2$O, separated, and the aqueous layer extracted with Et$_2$O. The combined organics were washed with H$_2$O and saturated NaCl, dried over Na$_2$SO$_4$, filtered, and concentrated to give a pale yellow solid (0.86 g, 79% yield). LCMS: MH$^+$=230.

Preparative Examples 35–53.16

By essentially the same procedure set forth in Preparative Example 34, only substituting the compound shown in Column 2 of Table 6, the compounds shown in Column 3 of Table 6 were prepared:

TABLE 6

| Prep. Ex. | Column 2 | Column 3 | DATA |
|---|---|---|---|
| 35 | 2-fluorophenyl pyrazolopyrimidinone | 2-fluorophenyl chloro-pyrazolopyrimidine | LCMS: MH+ = 248 |
| 36 | 2-chlorophenyl pyrazolopyrimidinone | 2-chlorophenyl chloro-pyrazolopyrimidine | |
| 37 | 3-CF3-phenyl pyrazolopyrimidinone | 3-CF3-phenyl chloro-pyrazolopyrimidine | LCMS: MH+ = 298 |
| 38 | isopropyl pyrazolopyrimidinone | isopropyl chloro-pyrazolopyrimidine | LCMS: MH+ = 196 |
| 39 | tert-butyl pyrazolopyrimidinone | tert-butyl chloro-pyrazolopyrimidine | LCMS: MH+ = 210 |
| 40 | phenyl, cyclopropyl pyrazolopyrimidinone | phenyl, cyclopropyl chloro-pyrazolopyrimidine | |
| 41 | phenyl, isopropyl pyrazolopyrimidinone | phenyl, isopropyl chloro-pyrazolopyrimidine | LCMS: MH+ = 272 |

TABLE 6-continued

| Prep. Ex. | Column 2 | Column 3 | DATA |
|---|---|---|---|
| 42 | | | |
| 43 | | | LCMS: MH$^+$ = 255 |
| 44 | | | |
| 45 | | | Yield = 65% LCMS: MH$^+$ = 260 |
| 46 | | | Yield = 35% LCMS: MH$^+$ = 290 |
| 47 | | | Yield = 32% LCMS: MH$^+$ = 298 |
| 48 | | | Yield = 45% LCMS: MH$^+$ = 236 |

TABLE 6-continued

| Prep. Ex. | Column 2 | Column 3 | DATA |
|---|---|---|---|
| 49 | | | Yield = 100%<br>LCMS:<br>MH$^+$ = 250 |
| 50 | | | Yield = 88%<br>LCMS:<br>MH$^+$ = 314 |
| 51 | | | Yield = 43%<br>LCMS:<br>MH$^+$ = 223 |
| 52 | | | Yield = 30%<br>LCMS:<br>MH$^+$ = 295 |
| 53 | | | Yield = 98%<br>LCMS:<br>MH$^+$ = 244 |
| 53.11 | | | |
| 53.12 | | | |

TABLE 6-continued

| Prep. Ex. | Column 2 | Column 3 | DATA |
|---|---|---|---|
| 53.13 | Cbz-piperidin-4-yl-pyrazolo[1,5-a]pyrimidin-7-ol | Cbz-piperidin-4-yl-7-chloropyrazolo[1,5-a]pyrimidine | Yield = 96<br>MH⁺ = 371 |
| 53.14 | Cbz-piperidin-3-yl-pyrazolo[1,5-a]pyrimidin-7-ol | Cbz-piperidin-3-yl-7-chloropyrazolo[1,5-a]pyrimidine | Yield = 99<br>MH⁺ = 371 |
| 53.15 | cyclohexyl-pyrazolo[1,5-a]pyrimidin-7-ol | cyclohexyl-7-chloropyrazolo[1,5-a]pyrimidine | Yield = quant.<br>MH⁺ = 236 |
| 53.16 | Boc-piperidin-3-yl-pyrazolo[1,5-a]pyrimidin-7-one | Boc-piperidin-3-yl-7-chloropyrazolo[1,5-a]pyrimidine | Yield = 71%.<br>MH⁺ = 337 |

Preparative Example 53.17

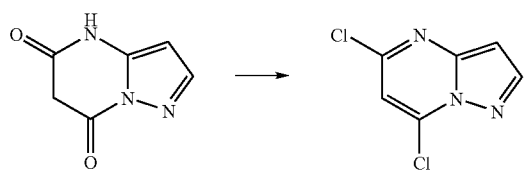

POCl₃ (62 mL) was cooled to 5° C. under nitrogen and dimethylaniline (11.4 g, 2.8 eq.) and the compound prepared in Preparative Example 33.10 (4.75 g, 0.032 mol). The reaction mixture was warmed to 60° C. and stirred overnight. The reaction mixture was cooled to 30° C. and the POCl₃ was distilled off under reduced pressure. The residue was dissolved in CH₂Cl₂ (300 mL) and poured onto ice. After stirring 15 minutes, the pH of the mixture was adjusted to 7-8 with solid NaHCO₃. The layers were separated and the organic layer was washed with H₂O (3×200 mL), dried over MgSO₄, filtered, and concentrated. The crude product was purified by flash chromatography using a 50:50 CH₂Cl₂: hexanes solution as eluent to elute the dimethyl aniline. The eluent was then changed to 75:25 CH₂Cl₂: hexanes to elute the desired product (4.58 g, 77% yield). MS: MH⁺=188.

Preparative Examples 53.18–53.19

By essentially the same procedure set forth in Preparative Example 53.17 only substituting the compound in Column 2 of Table 6.10, the compounds shown in Column 3 of Table 6.10 are prepared:

TABLE 6.10

| Prep. Ex. | Column 2 | Column 3 |
|---|---|---|
| 53.18 | 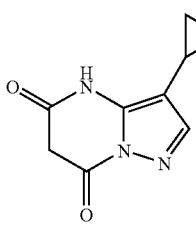 | 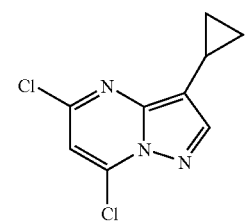 |
| 53.19 | 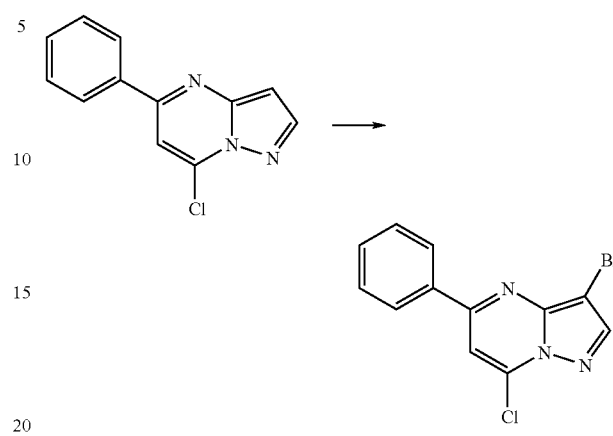 | 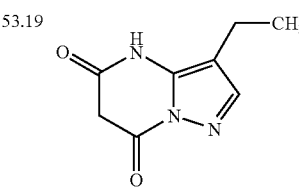 |

Preparative Example 54

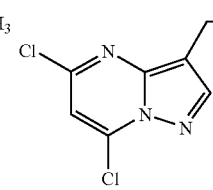

A solution of the compound prepared in Preparative Example 34 (0.10 g, 0.435 mmol) in CH$_3$CN (3 mL) was treated with N-bromosuccinimide ("NBS") (0.085 g, 1.1 eq.). The reaction mixture was stirred at room temperature 1 hour and concentrated under reduced pressure. The crude product was purified by flash chromatography using a 20% EtOAc-in-hexanes solution as eluent (0.13 g, 100% yield). LCMS: MH$^+$=308.

Preparative Examples 55–68.16

By essentially the same procedure set forth in Preparative Example 54 only substituting the compounds shown in Column 2 of Table 7, the compounds shown in Column 3 of Table 7 were prepared:

TABLE 7

| Prep. Ex. | Column 2 | Column 3 | DATA |
|---|---|---|---|
| 55 | 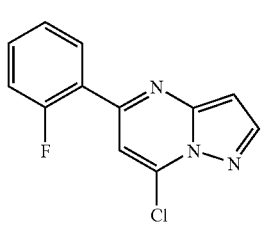 | 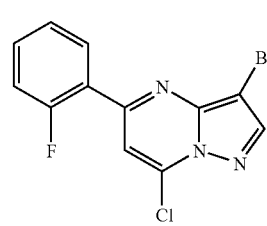 | LCMS: MH$^+$ = 326 |
| 56 | 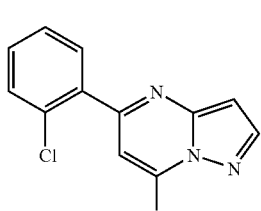 | 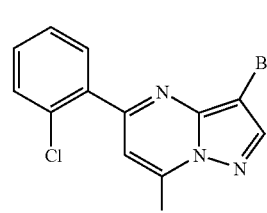 | LCMS: MH$^+$ = 342 |

TABLE 7-continued
| Prep. Ex. | Column 2 | Column 3 | DATA |
|---|---|---|---|
| 57 | 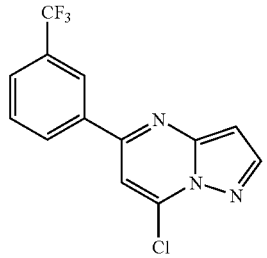 | 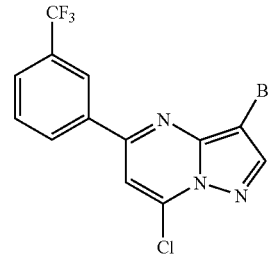 | LCMS: MH+ = 376 |
| 58 | 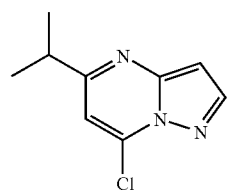 | 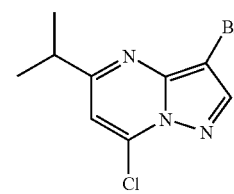 | LCMS: MH+ = 274 |
| 59 | 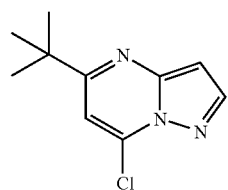 | 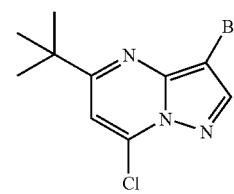 | LCMS: MH+ = 288 |
| 60 | 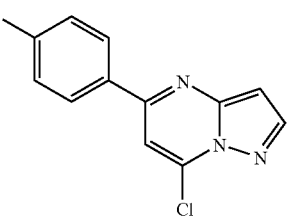 | 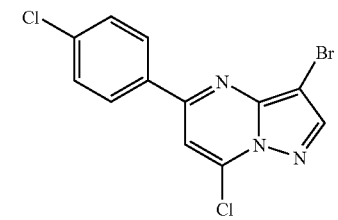 | |
| 61 | 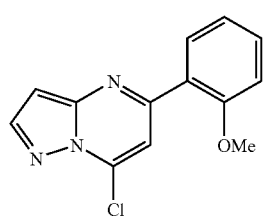 | 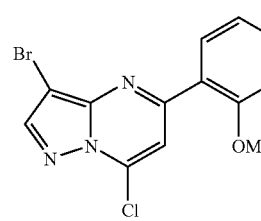 | Yield = 75% LCMS: MH+ = 338 |
| 62 | 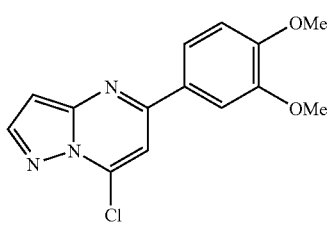 | 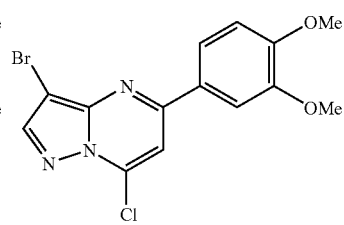 | Yield = 52% LCMS: MH+ = 368 |
| 63 | 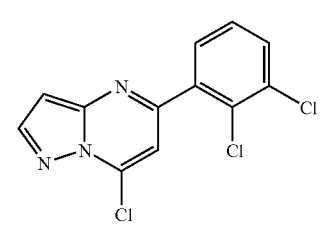 | 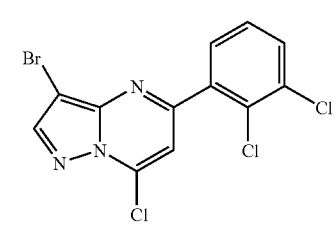 | Yield = 87% LCMS: MH+ = 376 |

TABLE 7-continued
| Prep. Ex. | Column 2 | Column 3 | DATA |
|---|---|---|---|
| 64 | 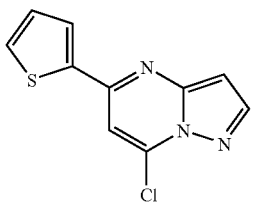 | 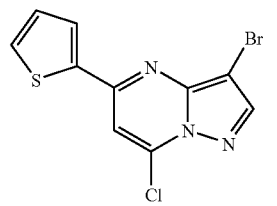 | Yield = 100%<br>LCMS:<br>MH⁺ = 316 |
| 65 | 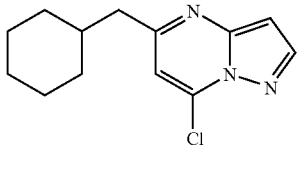 | 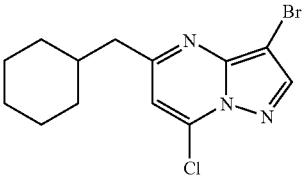 | Yield = 92%<br>LCMS:<br>MH⁺ = 330 |
| 66 | 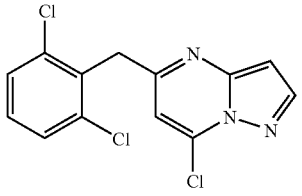 | 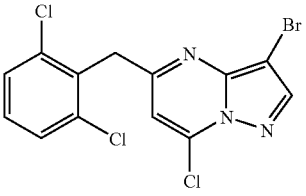 | Yield = 82%<br>LCMS:<br>MH⁺ = 395 |
| 67 | 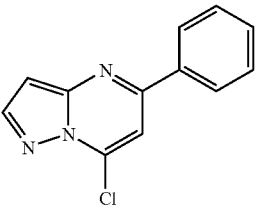 | 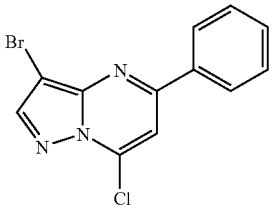 | Yield = 88%<br>LCMS:<br>MH⁺ = 308 |
| 68 | 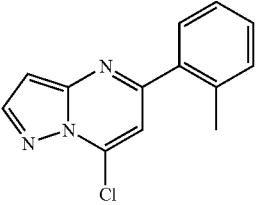 | 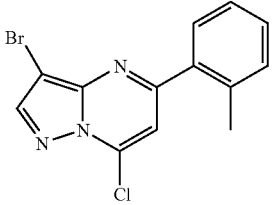 | Yield = 100%<br>LCMS:<br>MH⁺ = 322 |
| 68.10 | 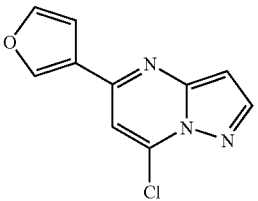 | 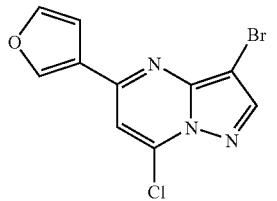 | |
| 68.11 | 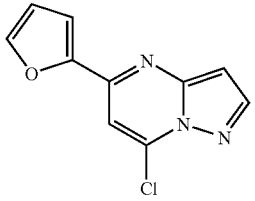 | 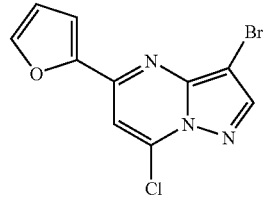 | |

TABLE 7-continued

| Prep. Ex. | Column 2 | Column 3 | DATA |
|---|---|---|---|
| 68.12 | Cbz-N-piperidinyl-pyrazolo[1,5-a]pyrimidine-Cl | Cbz-N-piperidinyl-3-Br-pyrazolo[1,5-a]pyrimidine-Cl | Yield = 99  MH+ = 449 |
| 68.13 | Cbz-N-piperidin-3-yl-pyrazolo[1,5-a]pyrimidine-Cl | Cbz-N-piperidin-3-yl-3-Br-pyrazolo[1,5-a]pyrimidine-Cl | Yield = 95  MH+ = 449 |
| 68.14 | 5,7-dichloropyrazolo[1,5-a]pyrimidine | 3-bromo-5,7-dichloropyrazolo[1,5-a]pyrimidine | MH+ = 266 |
| 68.15 | cyclohexyl-pyrazolo[1,5-a]pyrimidine-Cl | cyclohexyl-3-Br-pyrazolo[1,5-a]pyrimidine-Cl | Yield = quant.  MH+ = 314 |
| 68.16 | Boc-N-piperidin-3-yl-pyrazolo[1,5-a]pyrimidine-Cl | Boc-N-piperidin-3-yl-3-Br-pyrazolo[1,5-a]pyrimidine-Cl | Yield = 97%  MH+ = 417 |

Preparative Example 69

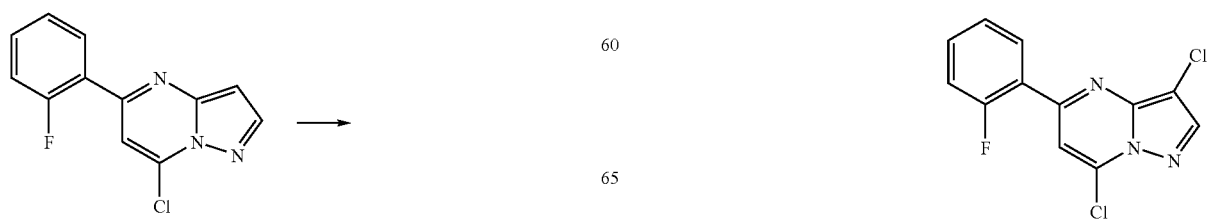

-continued

A solution of the compound prepared in Preparative Example 35 (0.3 g, 1.2 mmol) in CH₃CN (15 mL) was treated with NCS (0.18 g, 1.1 eq.) and the resulting solution heated to reflux 4 hours. Additional NCS (0.032 g, 0.2 eq.) added and the resulting solution was stirred at reflux overnight. The reaction mixture was cooled to room temperature, concentrated in vacuo and the residue purified by flash chromatography using a 20% EtOAc in hexanes solution as eluent (0.28 g, 83% yield). LCMS: MH$^+$=282.

Preparative Example 70

By essentially the same procedure set forth in Preparative Example 69 only substituting the compound shown in Column 2 of Table 8, the compound shown in Column 3 of Table 8 was prepared:

TABLE 8

| Prep. Ex. | Column 2 | Column 3 | DATA |
|---|---|---|---|
| 70 |  | 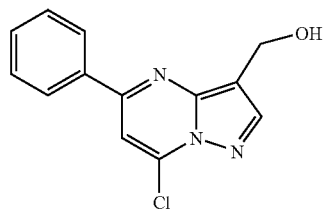 | Yield = 82%<br>LCMS:<br>MH$^+$ = 286 |

Preparative Example 71

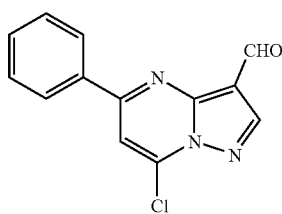

To a solution of the compound from Preparative Example 34 (1.0 g, 4.35 mmol) in DMF (6 mL) was added POCl₃ (1.24 mL, 3.05 eq.) and the resulting mixture was stirred at room temperature overnight. The reaction mixture was cooled to 0° C. and the excess POCl₃ was quenched by the addition of ice. The resulting solution was neutralized with 1N NaOH, diluted with H₂O, and extracted with CH₂Cl₂. The combined organics were dried over Na₂SO₄, filtered and concentrated in vacuo. The crude product was purified by flash chromatography using a 5% MeOH in CH₂Cl₂ solution as eluent (0.95 g, 85% yield). LCMS: MH$^+$=258.

Preparative Example 72

-continued

To a solution of the product of Preparative Example 71 (0.25 g, 0.97 mmol) in THF was added NaBH₄ (0.041 g, 1.1 eq.) and the resulting solution was stirred at room temperature overnight. The reaction mixture was quenched by the addition of H₂O and extracted with CH₂Cl₂. The combined organics were dried over Na₂SO₄, filtered, and concentrated under reduced pressure. The crude product was purified by flash chromatography using a 60:40 hexanes: EtOAc mix as eluent (0.17 g, 69% yield). LCMS: MH$^+$=260.

Preparative Example 73

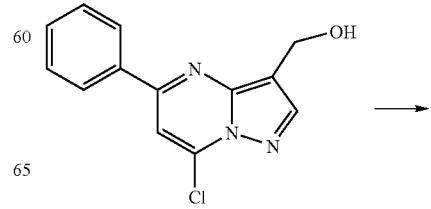

-continued

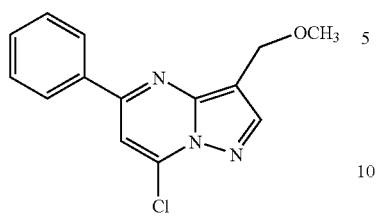

A solution of the compound prepared in Preparative Example 72 (0.12 g, 0.462 mmol), dimethyl sulfate (0.088 mL, 2.0 eq), 50% NaOH (0.26 mL) and catalytic Bu$_4$NBr in CH$_2$Cl$_2$ (4 mL) was stirred at room temperature overnight. The reaction mixture was diluted with H$_2$O and extracted with CH$_2$Cl$_2$. The combined organics were dried over Na$_2$SO$_4$, filtered, and concentrated under reduced pressure. The crude product was purified by flash chromatography using a 30% EtOAc-in-hexanes solution as eluent (0.062 g, 48% yield).

Preparative Example 74

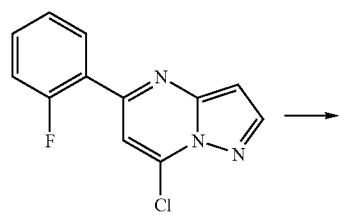

The compound prepared in Preparative Example 35 (0.3 g, 1.2 mmol), K$_2$CO$_3$ (0.33 g, 2 eq.), and 4-aminompyridine (1.1 eq.) are reacted in 5 mL CH$_3$CN for two days and concentrated under reduced pressure. The residue is partitioned between H$_2$O and CH$_2$Cl$_2$. The organic layer is dried over Na$_2$SO$_4$, filtered and, concentrated. The crude product is purified by flash chromatography using a 5% (10% NH$_4$OH in MeOH) solution in CH$_2$Cl$_2$ as eluent to give the desired product.

Preparative Example 75

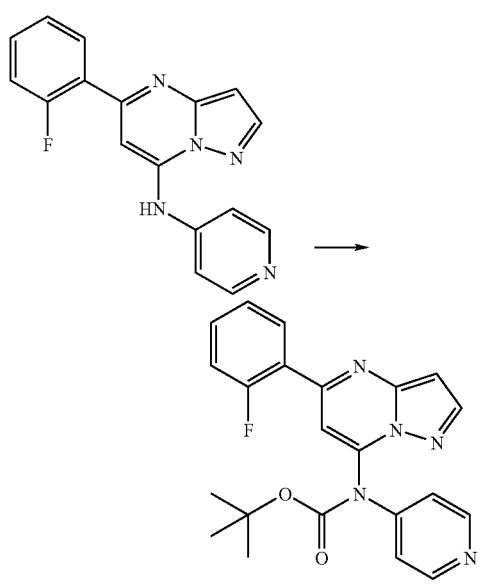

The compound from Preparative Example 74 (0.91 mmol), BOC$_2$O (0.22 g, 1.1 eq), and DMAP (0.13 g, 1.1 eq.) are reacted in dioxane (10 mL) at room temperature for 3 days. Additional BOC$_2$O (0.10 g, 0.5 eq.) is added and stirred for 4 hours. It is then concentrated in vacuo, diluted with saturated NaHCO$_3$ (15 mL), and extracted with CH$_2$Cl$_2$ (2×100 mL). The combined organic layers are dried over Na$_2$SO$_4$, filter, and concentrate under reduced pressure. The crude product is purified by flash chromatography using a 5% (10% NH$_4$OH in MeOH) solution in CH$_2$Cl$_2$ as eluent to give the product.

Preparative Example 76

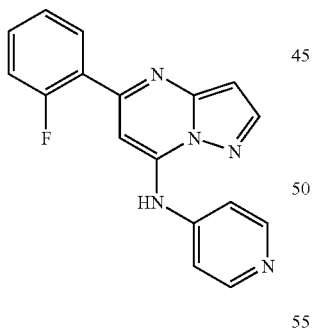

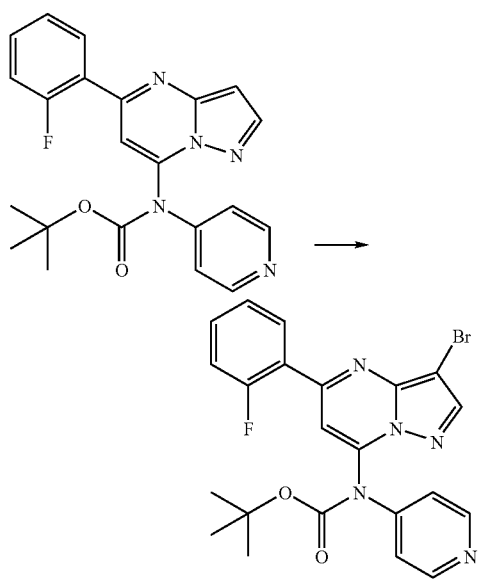

By essentially the same procedure set forth in Preparative Example 54 only substituting the compound prepared in Preparative Example 75, the above product is prepared.

Preparative Example 77

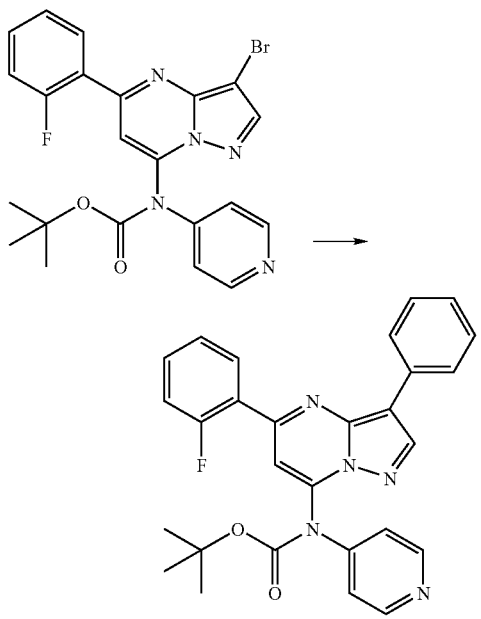

The product of Preparative Example 76 (0.3 mmol), phenylboronic acid (0.073 g, 2.0 eq.), K₃PO₄ (0.19 g, 3.0 eq.), and Pd(PPh₃)₄ (0.017 g, 5 mol %) are reacted in refluxing DME (16 mL) and H₂O (4 mL) for 7 hours. The resulting solution is cooled to room temperature, diluted with H₂O (10 mL), and extracted with CH₂Cl₂ (3×50 mL). The combined organics are dried over Na₂SO₄, filtered, and concentrated. The crude product is purified by flash chromatography using a 2.5% (10% NH₄OH in MeOH) in CH₂Cl₂ solution as eluent to obtain the product.

Preparative Example 78

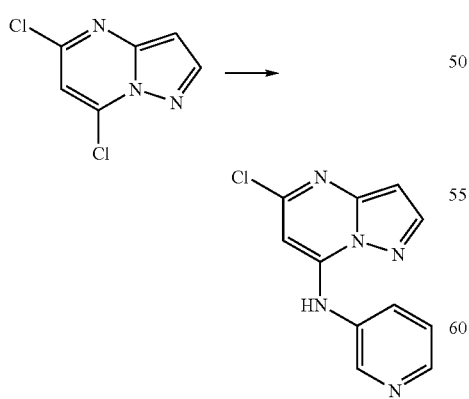

To a solution of the compound prepared in Preparative Example 53.17 (0.25 g, 1.3 mmol) in dioxane (5 mL) is added iPr₂NEt (0.47 mL, 2.0 eq.) and 3-aminomethylpyridine (0.15 ml, 1.1 eq.). The resulting solution is stirred at room temperature 72 hours. The reaction mixture is diluted with H₂O and extracted with EtOAc. The combined organics are washed with H₂O and saturated NaCl, dried over Na₂SO₄, filtered, and concentrated in vacuo. The crude product is purified by flash chromatography.

Preparative Examples 79–81

By essentially the same procedure set forth in Preparative Example 78 only substituting the compound shown in Column 2 of Table 8.10, the compounds shown in Column 3 of Table 8.10 are prepared.

TABLE 8.10

| Prep. Ex. | Column 2 | Column 3 |
|---|---|---|
| 79 | | ![](Cl-pyrazolopyrimidine-NH-4-pyridyl) |
| 80 | | ![](Cl-3-Br-pyrazolopyrimidine-NH-3-pyridyl) |
| 81 | | ![](Cl-3-Br-pyrazolopyrimidine-NH-4-pyridyl) |

Preparative Example 82

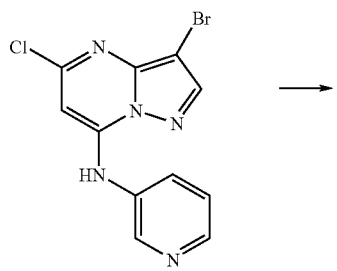

-continued

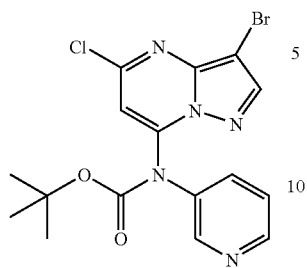

By essentially the same procedure set forth in Preparative Example 75 only substituting the compound from Preparative Example 80, the above compound is prepared.

Example 1

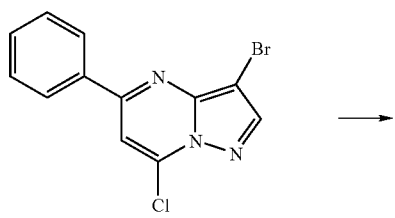

-continued

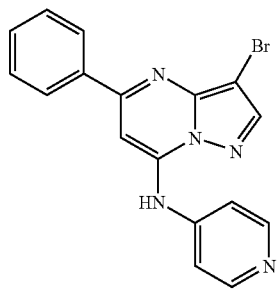

The product from Preparative Example 54 (0.875 mmol), 4-aminopyridine (0.12 g, 1.3 eq.), and $K_2CO_3$ (0.24 g, 2 eq.) are reacted in $CH_3CN$ (5 mL) as described in Preparative Example 74 to obtain the product.

Examples 2–46.18

By following essentially the same procedure described in Example 1 only using the reactants shown in Columns 2 and 3 of Table 9, the products shown in Column 4 can be obtained.

TABLE 9

| Ex. | Column 2 | Column 3 | Column 4 |
|---|---|---|---|
| 2 | | | |
| 3 | | | |

TABLE 9-continued

| Ex. | Column 2 | Column 3 | Column 4 |
| --- | --- | --- | --- |
| 4 | | | |
| 5 | | | |
| 6 | | | |
| 7 | | | |
| 8 | | | |

TABLE 9-continued

| Ex. | Column 2 | Column 3 | Column 4 |
|---|---|---|---|
| 9 | | | |
| 10 | | | |
| 11 | | | |
| 12 | | | |
| 13 | | | |

TABLE 9-continued
| Ex. | Column 2 | Column 3 | Column 4 |
|---|---|---|---|
| 14 | 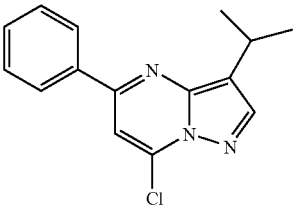 | 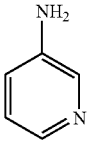 | 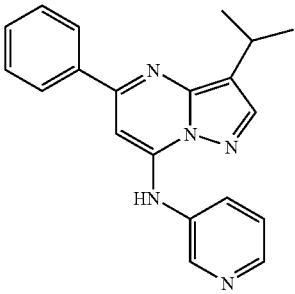 |
| 15 | 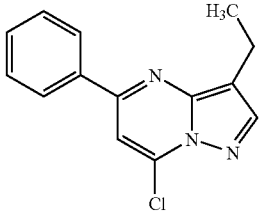 | 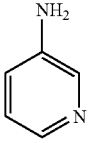 | 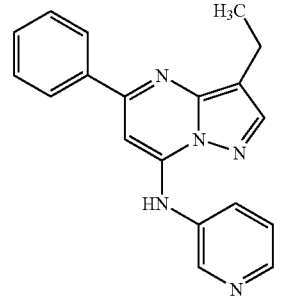 |
| 16 | 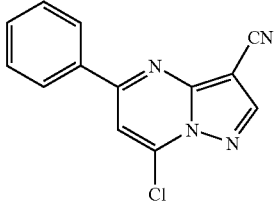 | 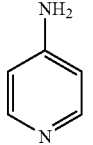 | 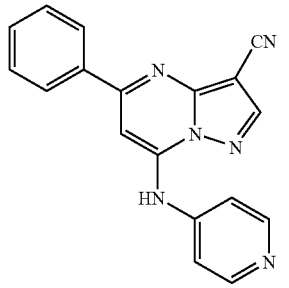 |
| 17 | 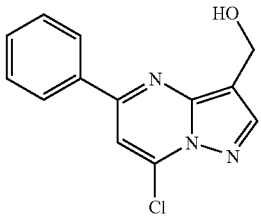 | 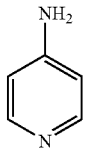 | 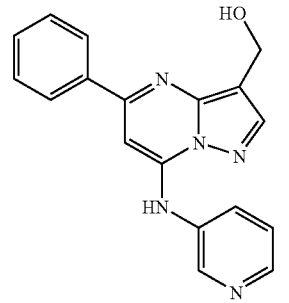 |
| 18 | 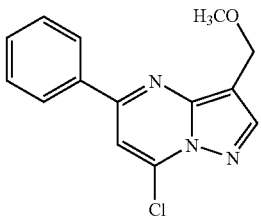 | 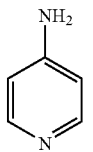 | 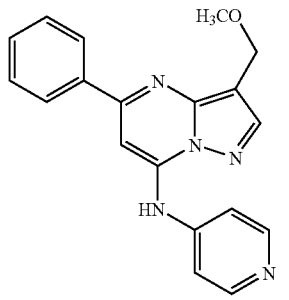 |

TABLE 9-continued

| Ex. | Column 2 | Column 3 | Column 4 |
| --- | --- | --- | --- |
| 19 | | | |
| 20 | | | |
| 21 | | | |
| 22 | | | |

TABLE 9-continued
| Ex. | Column 2 | Column 3 | Column 4 |
|---|---|---|---|
| 23 | 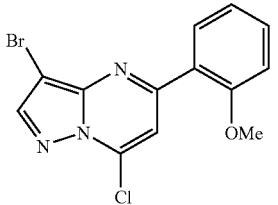 | 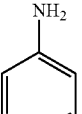 | 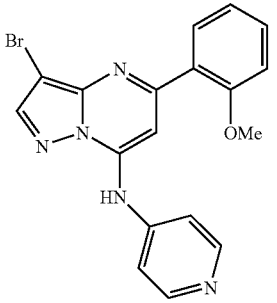 |
| 24 | 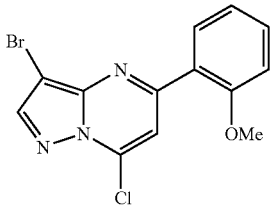 |  | 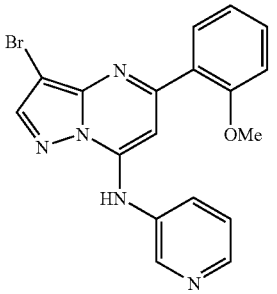 |
| 25 | 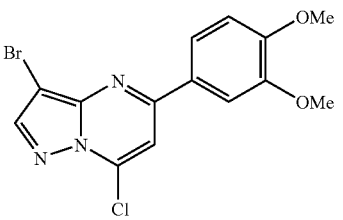 |  | 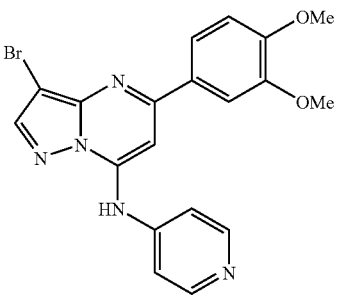 |
| 26 | 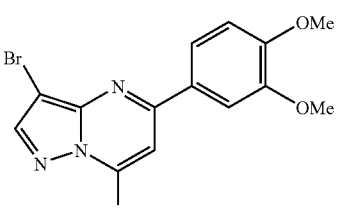 |  | 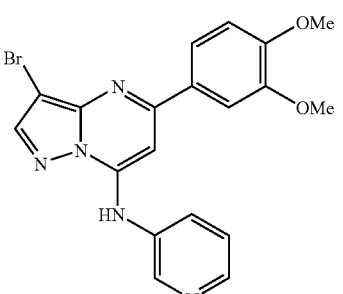 |
| 27 | 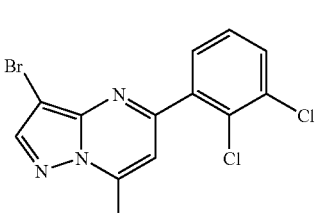 | 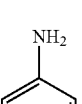 | 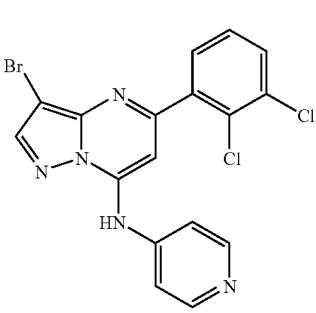 |

TABLE 9-continued

| Ex. | Column 2 | Column 3 | Column 4 |
|-----|----------|----------|----------|
| 28 | | | |
| 29 | | | |
| 30 | | | |
| 31 | | | |

TABLE 9-continued

| Ex. | Column 2 | Column 3 | Column 4 |
|---|---|---|---|
| 32 | | | |
| 33 | | | |
| 34 | | | |
| 35 | | | |
| 36 | | | |

TABLE 9-continued

| Ex. | Column 2 | Column 3 | Column 4 |
| --- | --- | --- | --- |
| 37 | | | |
| 38 | | | |
| 39 | | | |
| 40 | | | |
| 41 | | | |

TABLE 9-continued
| Ex. | Column 2 | Column 3 | Column 4 |
| --- | --- | --- | --- |
| 42 | 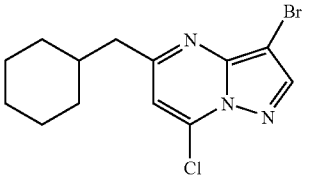 | 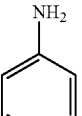 | 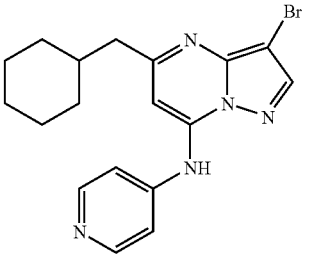 |
| 43 | 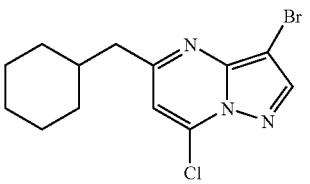 | 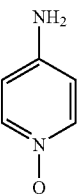 | 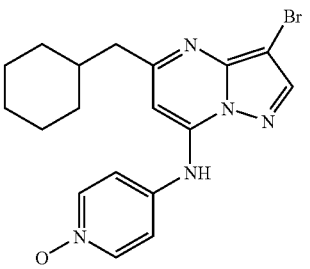 |
| 44 | 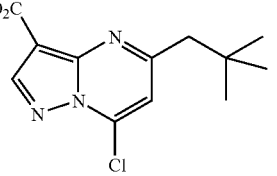 | 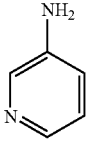 | 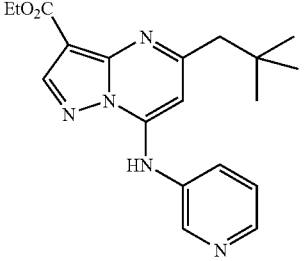 |
| 45 | 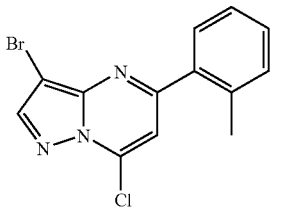 | 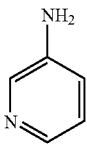 | 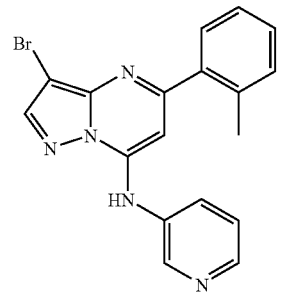 |
| 46 | 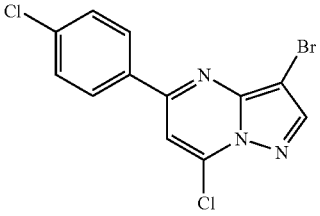 | 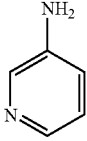 | 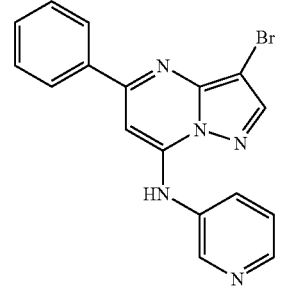 |

TABLE 9-continued
| Ex. | Column 2 | Column 3 | Column 4 |
| --- | --- | --- | --- |
| 46.10 | 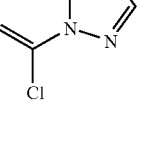 | 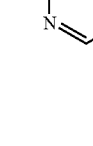 | 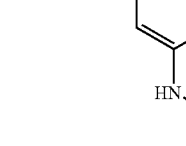 |
| 46.11 | 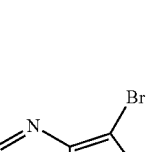 | 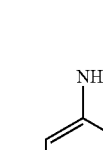 | 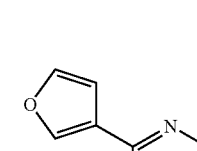 |
| 46.12 | 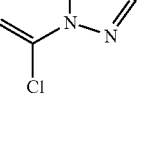 | 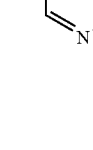 | 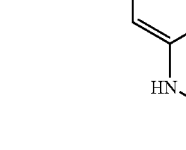 |
| 46.13 | 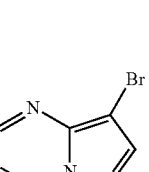 | 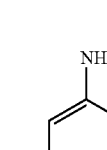 | 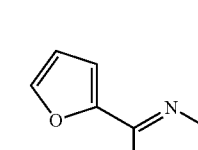 |
| 46.14 | 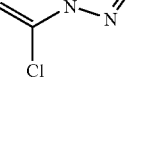 |  | 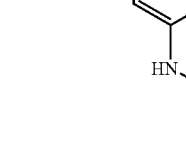 |

TABLE 9-continued

| Ex. | Column 2 | Column 3 | Column 4 |
|---|---|---|---|
| 46.15 | | | |
| 46.16 | | | |
| 46.17 | | | |
| 46.18 | | | |

103

Example 47

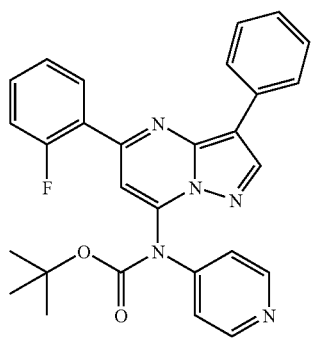

→

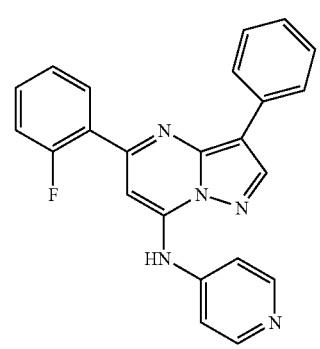

TFA (0.5 mL) was added to a solution of the compound prepared in Preparative Example 76 (0.16 mmol) in CH₂Cl₂ (2.0 mL) at 0° C. and the solution stirred for 2.5 hours. It was stored at 4° C. overnight at which time an additional TFA (0.5 mL) is added. It was stirred for 4 hours and concentrated in vacuo. It was neutralized with 1N NaOH and extracted with CH₂Cl₂. The combined organic layers were dried over Na₂SO₄, filter, and concentrated under reduced pressure. The crude product was purified by flash chromatography using a 2.5% (10% NH₄OH in MeOH) in CH₂Cl₂ solution as eluent to give the product.

Example 48

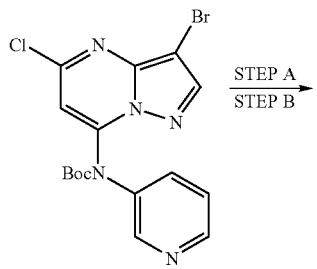

STEP A
STEP B
→

104

-continued

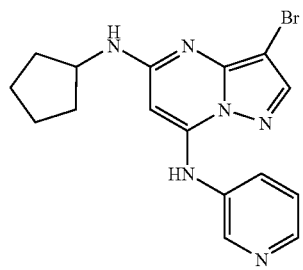

Step A:

To a solution of 5-chloro adduct in dioxane/DIPEA (2.5/1.0) at rt is added cyclopentylamine (1.2 eq.) dropwise. The resulting solution is stirred at reflux for 16 h, cooled to rt, and concentrated under reduced pressure. The crude material is purified by preparative thin-layer chromatography (8×1000 μM).

Step B:

To a solution of the compound prepared in Example 48, Step A in CH₂Cl₂ at rt is added TFA (5 eq.) dropwise. The resulting solution is stirred for 18 h at rt and is concentrated under reduced pressure. The crude material is redissolved in CH₂Cl₂ and the organic layer is sequentially washed with sat. aq. NaHCO₃ (2×2 mL) and brine (1×2 mL). The organic layer is dried (Na₂SO₄), filtered, and concentrated under reduced pressure. The crude material is purified by preparative thin-layer chromatography (8×1000 μM).

Examples 49–58

By essentially the same procedure set forth in Example 48 only substituting the chlorides in Column 2 of Table 10 the compounds shown in Column 3 of Table 10 are prepared.

TABLE 10

| Ex. | Column 2 | Column 4 |
|---|---|---|
| 49 | cyclohexyl-NH₂ | cyclohexyl-NH-[3-bromo-pyrazolo[1,5-a]pyrimidine]-NH-pyridin-3-yl |
| 50 | (S)-2-(hydroxymethyl)pyrrolidine | (S)-2-(hydroxymethyl)pyrrolidin-1-yl-[3-bromo-pyrazolo[1,5-a]pyrimidine]-NH-pyridin-3-yl |

TABLE 10-continued
| Ex. | Column 2 | Column 4 |
|---|---|---|
| 51 | | |
| 52 | | |
| 53 | | |
| 54 | | |
| 55 | | |
| 56 | | |
| 57 | | |
| 58 | | |
Example 59
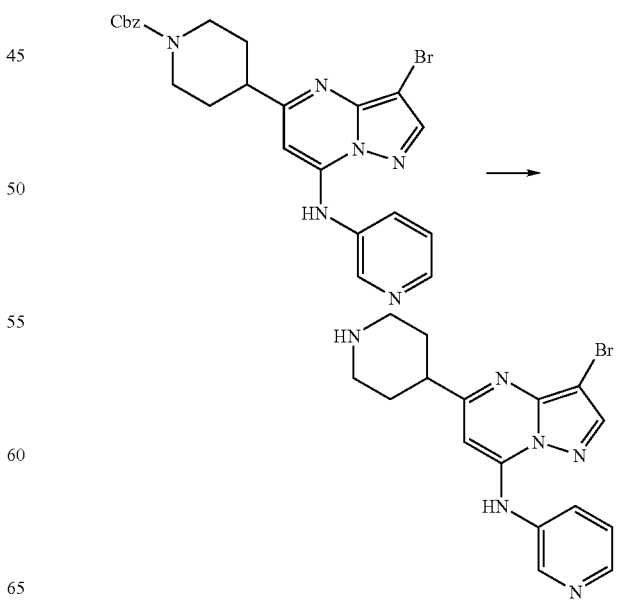

To a solution of the compound prepared in Example 46.14 in anhydrous acetonitrile is added TMSI (4 eq.), dropwise at ambient temperature. After 10 minutes the acetonitrile is removed in vacuo. The resulting yellow foam is treated with 2 N HCl solution (7 mL) and then washed immediately with Et$_2$O (5×). The pH of the aqueous is adjusted to 10 with 50% NaOH (aq) and the product is isolated by saturation of the solution with NaCl (s) followed by extraction with CH$_2$Cl$_2$ (5×) to give the desired product.

Examples 60–62

By essentially the same procedure set forth in Example 58 only substituting the compounds shown in Column 2 of Table 11, the compounds shown in Column 3 of Table 11 were prepared.

Preparative Example 83

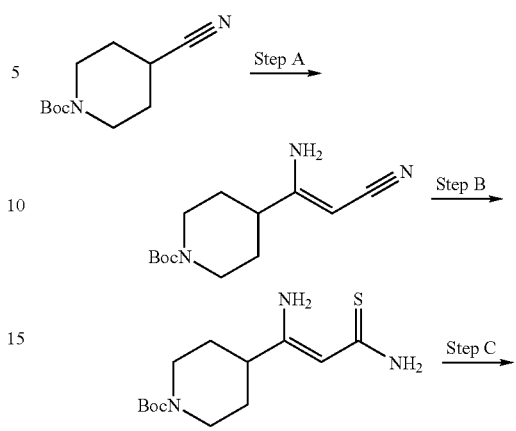

TABLE 11

| Ex. | Column 2 | Column 3 |
|---|---|---|
| 60 | | |
| 61 | | |
| 62 | | |

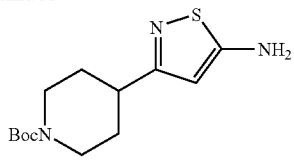

Step A 4-(1-Amino-2-cyano-vinyl)-piperidine-1-carboxylic acid tert-butyl ester was prepared from 4-cyano-piperidine-1-carboxylic acid tert-butyl ester (10.0 mmol scale) according to the procedure described in WO 2004/014910 A1 (p. 32). The crude residue was used in Step B without purification.

Step B

A solution of crude 4-(1-Amino-2-cyano-vinyl)-piperidine-1-carboxylic acid tert-butyl ester in 1/1 THF/ethanol (10 mL) was cooled to 0° C. and treated with hydrogen sulfide gas for ca. 5 min. The tube was sealed and heated at 85° C. for 4 hr. The reaction vessel was cooled in an ice-bath, carefully vented and the reaction mixture was concentrated. The crude residue was used in Step C without further purification.

Step C

To the crude residue from Part B and potassium carbonate (2.1 g, 15.0 mmol) in diethyl ether (15 mL) at rt was added dropwise a solution of iodine (1.02 g, 4.0 mmol) in ether (6 mL). The mixture was stirred at rt for an additional 2 hr. Water and ethyl acetate were added. The aqueous phase was washed with ethyl acetate and the combined organic extracts were washed with water, brine and dried (sodium sulfate). Purification of the residue by chromatography (40% ethyl acetate in hexanes) afforded 250 mg of 4-(5-amino-isothiazol-3-yl)-piperidine-1-carboxylic acid tert-butyl ester (9% yield based on 4-cyano-piperidine-1-carboxylic acid tert-butyl ester). LCMS: $(M-C_4H_8)^+ = 228.1$.

Preparative Example 84

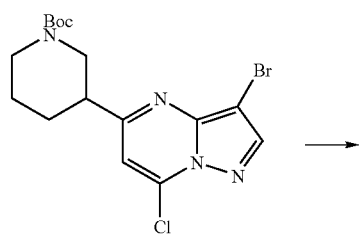

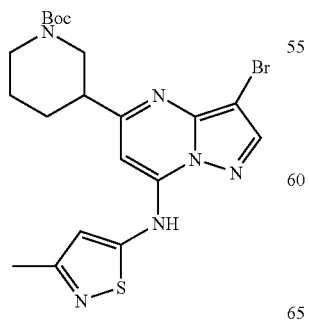

To a solution of 5-amino-3-methyl isothiazole hydrochloride (0.29 g, 1.92 mmol) in DMSO (2.5 mL) at rt was added NaH (92 mg, 3.85 mmol) portionwise. The mixture was stirred for 15 min at rt whereupon the 7-Cl adduct (0.40 g, 0.96 mmol) from Preparative Example 68.16 in DMSO (3 mL) was added dropwise. The mixture was stirred for 12 h at rt and was treated with sat. aq. $NH_4Cl$ (5 mL). The mixture was extracted with 10% $IPA/CH_2Cl_2$ (3×10 mL) and the organic layers were combined. The organic layer was dried ($Na_2SO_4$), filtered and concentrated under reduced pressure. The crude product was diluted with water (2 mL) and the resultant precipitate ("ppt") was filtered off. The ppt was washed with cold water (2×2 mL) and was dried under high vacuum to afford 0.45 g (95%). LC-MS: 495.3 [M+H] 80% purity.

Preparative Example 84.10

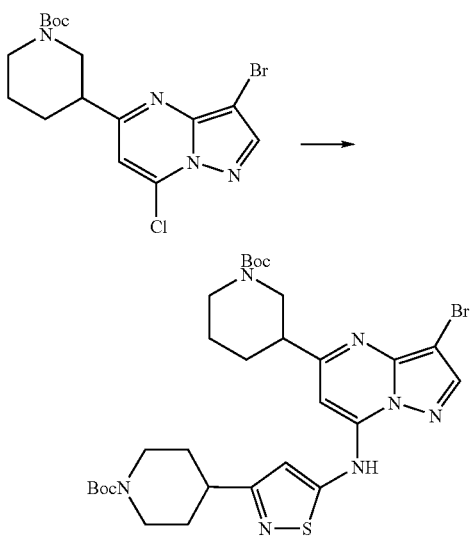

Utilizing the procedure set forth in Preparative Example 84, treatment of the Boc derivative from Preparative Example 68.16 with the amine from Preparative Example 83 would afford the title compound.

Preparative Example 85

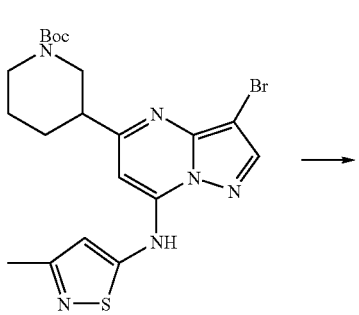

-continued

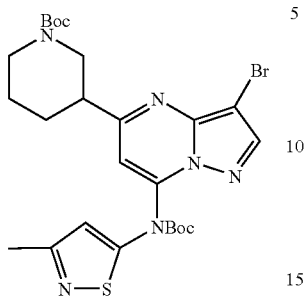

To a solution of 3-Br adduct (0.49 g, 0.99 mmol) from Preparative Example 84 in CH$_2$Cl$_2$ (2 mL) at rt was added Boc$_2$O (0.64 g, 2.97 mmol) followed by Et$_3$N (0.17 mL, 1.2 mmol) and DMAP (0.15 g, 1.2 mmol). The resulting solution was stirred for 16 h and brine (1 mL) was added. The layers were separated and the aqueous layer was extracted with CH$_2$Cl$_2$ (3×2 mL). The organic layers were combined, dried (Na$_2$SO$_4$), filtered, and concentrated under reduced pressure. The crude product was purified by preparative thin-layer chromatography (6×1000 μM plates) using a 3:1 mixture of hexanes/EtOAc as eluent to afford (0.31 g, 53% yield) as a brown solid. LC-MS: =595.3 [M+H] 99% purity.

Preparative Example 85.10

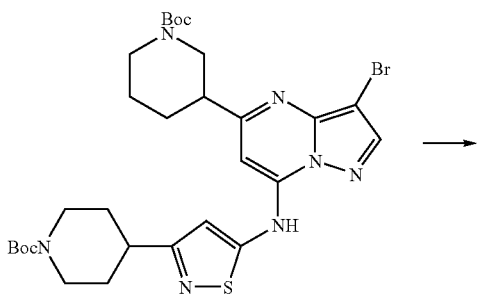

Utilizing the procedure set forth in Preparative Example 85, treatment of the Boc derivative from Preparative Example 84.10 would afford the title compound.

Preparative Example 86

To a mixture of Boc derivative (0.30 g, 0.51 mmol) from Preparative Example 85 in DME/H$_2$O (3 mL/1 mL) was added 1-methyl-4-(4,4,5,5-tetramethyl-1,3,2-dioxaborolan-2yl)-1H-pyrazole (0.21 g, 1.0 mmol) and K$_3$PO$_4$ (0.32 g, 1.53 mmol). N$_2$ was bubbled thru the solution for 20 min with stirring whereupon PdCl$_2$(dppf) (42 mg, 0.051 mmol) was added. The mixture was heated to 110° C. and was stirred for 12 h. The mixture was cooled to rt, concentrated under reduced pressure and placed under high vacuum. The crude product was purified by preparative thin-layer chromatography (6×1000 μM plates) using a 25:1 mixture of CH$_2$Cl$_2$/MeOH as eluent to afford (90 mg, 44% yield) as a orange semisolid. LC-MS: =595.1 [M+H] 85% purity.

Preparative Example 86.10

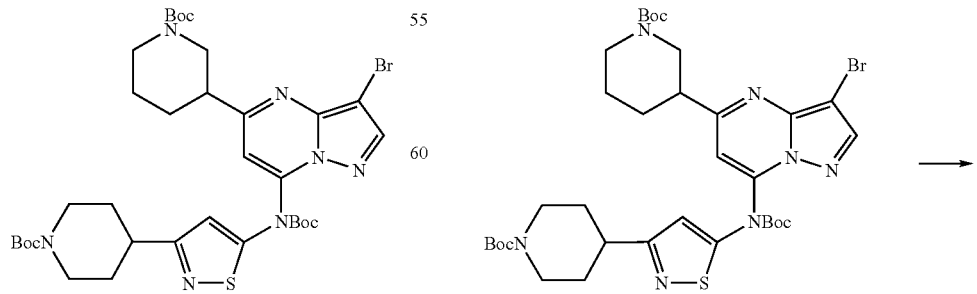

-continued

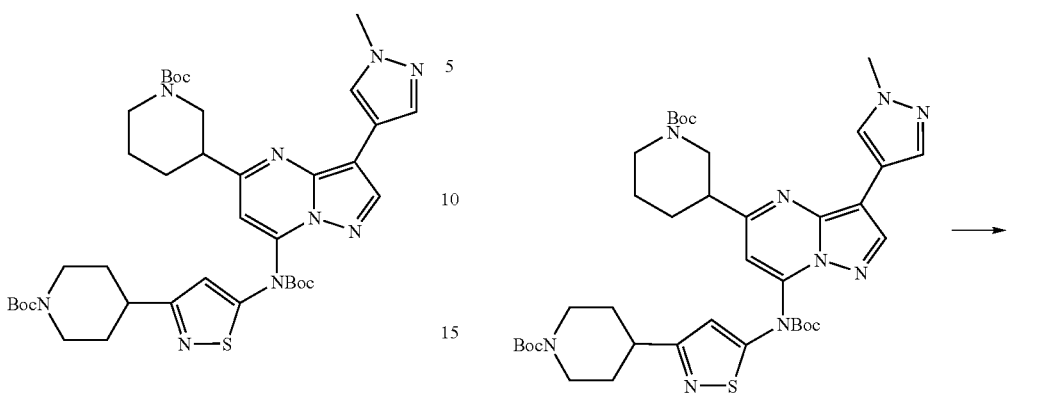

Utilizing the procedure set forth in Preparative Example 86, treatment of the Boc derivative from Preparative Example 85.10 would afford the title compound.

Example 84

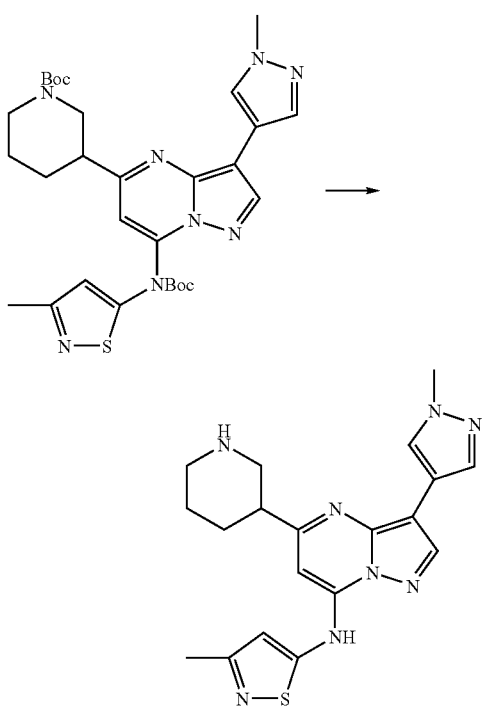

To a mixture of pyrazole adduct (50 mg, 0.084 mmol) from Preparative Example 86 in $CH_2Cl_2$ (2 mL) at 0° C. was added TFA (0.6 mL) dropwise. The resulting mixture was stirred for 12 h at rt and concentrated under reduced pressure. The crude material was dissolved in 7M $NH_3$ in MeOH (3 mL) and was stirred for 2 h. The mixture was concentrated under reduced pressure and placed under high vacuum. The crude product was purified by preparative thin-layer chromatography (4×1000 µM plates) using a 10:1 mixture of $CH_2Cl_2$/MeOH (7M $NH_3$) as eluent to afford (10 mg, 30% yield) as maize solid. mp 167–170° C.: LC-MS: =395.2 [M+H] 95%purity.

Example 84.10

Utilizing the procedure set forth in Example 84, treatment of the Boc derivative from Preparative Example 86.10 would afford the title compound.

ASSAY: The assay on the compounds of the present invention may be performed as follows.

BACULOVIRUS CONSTRUCTIONS: Cyclin E is cloned into pVL1393 (Pharmingen, La Jolla, Calif.) by PCR, with the addition of 5 histidine residues at the amino-terminal end to allow purification on nickel resin. The expressed protein is approximately 45 kDa. CDK2 is cloned into pVL1393 by PCR, with the addition of a haemaglutinin epitope tag at the carboxy-terminal end (YDVPDYAS). The expressed protein is approximately 34 kDa in size.

ENZYME PRODUCTION: Recombinant baculoviruses expressing cyclin E and CDK2 are co-infected into SF9 cells at an equal multiplicity of infection (MOI=5), for 48 hrs. Cells are harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates are spun down at 15000 RPM for 10 minutes and the supernatant retained. 5 ml of nickel beads (for one liter of SF9 cells) are washed three times in lysis buffer (Qiagen GmbH, Germany). Imidazole is added to the baculovirus supernatant to a final concentration of 20 mM, then incubated with the nickel beads for 45 minutes at 4° C. Proteins are eluted with lysis buffer containing 250 mM imidazole. Eluate is dialyzed overnight in 2 liters of kinase buffer containing 50 mM Tris pH 8.0, 1 mM DTT, 10 mM MgCl2, 100 uM sodium orthovanadate and 20% glycerol. Enzyme is stored in aliquots at −70° C.

IN VITRO KINASE ASSAY: Cyclin E/CDK2 kinase assays are performed in low protein binding 96-well plates (Corning Inc, Corning, N.Y.). Enzyme is diluted to a final concentration of 50 μg/ml in kinase buffer containing 50 mM Tris pH 8.0, 10 mM MgCl$_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Compounds are diluted in 10% DMSO to desirable concentrations. For each kinase reaction, 20 μl of the 50 μg/ml enzyme solution (1 μg of enzyme) and 20 μl of the 2 μM substrate solution are mixed, then combined with 10 μl of diluted compound in each well for testing. The kinase reaction is started by addition of 50 μl of 2 μM ATP and 0.1 μCi of 33P-ATP (from Amersham, UK). The reaction is allowed to run for 1 hour at room temperature. The reaction is stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal is then measured using a TopCount 96 well liquid scintillation counter (from Packard/Perkin Elmer Life Sciences).

IC$_{50}$ DETERMINATION: Dose-response curves are be plotted from inhibition data generated, each in duplicate, from 8 point serial dilutions of inhibitory compounds. Concentration of compound is plotted against % kinase activity, calculated by CPM of treated samples divided by CPM of untreated samples. To generate IC$_{50}$ values, the dose-response curves are then fitted to a standard sigmoidal curve and IC$_{50}$ values are derived by nonlinear regression analysis.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula:

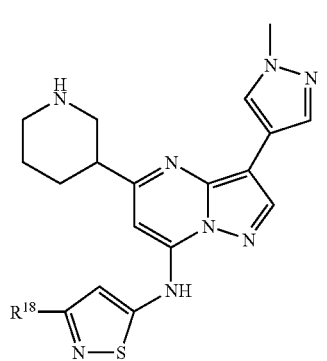

wherein R$^{18}$ is an alkyl or heterocyclyl with said heterocyclyl being linked to the isothiazole ring shown in the formula above via a carbon atom on said heterocyclyl, or a pharmaceutically acceptable salt, solvate, ester or prodrug of said compound.

2. The compound of claim 1, wherein R$^{18}$ is methyl.

3. The compound of claim 1, wherein said heterocyclyl is selected from the group consisting of:

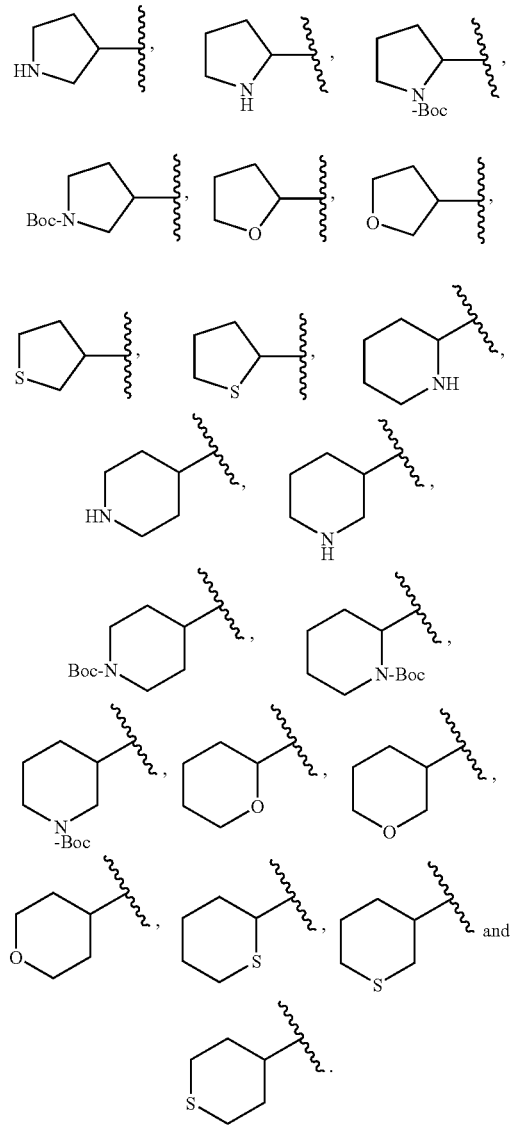

4. The compound of claim 3, wherein said heterocyclyl is:

5. A compound of formula:

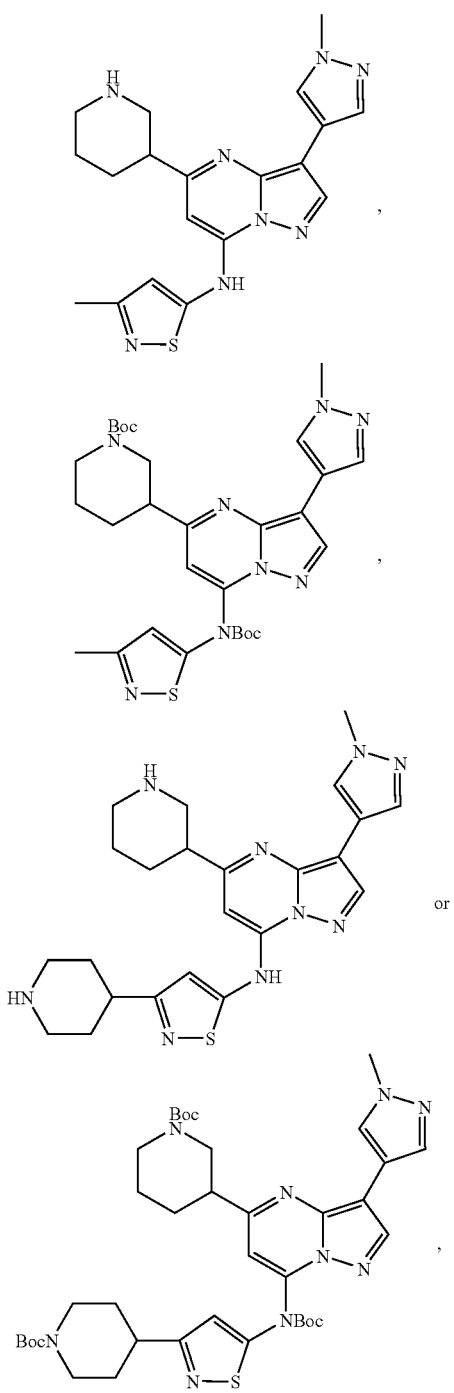

or a pharmaceutically acceptable salt, solvate, ester or prodrug of said compound.

6. A method of inhibiting cyclin dependent kinases2 (CDK2) in a patient, comprising administering a therapeutically effective amount of the compound of claim 1, or a pharmaceutically acceptable salt, solvate, ester or prodrug thereof, to said patient.

7. A pharmaceutical composition comprising a therapeutically effective amount of the compound of claim 1, or a pharmaceutically acceptable salt, ester or prodrug thereof, in combination with at least one pharmaceutically acceptable carrier.

8. The pharmaceutical composition of claim 7, additionally comprising one or more anti-cancer agents selected from the group consisting of cytostatic agent, taxótere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA® (gefitinib), TARCEVA® (erlotinib hydrochloride) antibodies to EGFR, GLEEVEC® (imatinib), intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, ERBITUX® (cetuximab), Liposomal, Thiotepa, Altretamine, Melphalan, Trastuzumab, Lerozole, Fulvestrant, Exemestane, Fulvestrant, Ifosfomide, Rituximab, C225, and Campath.

9. A method of inhibiting cyclin dependent kinases2 (CDK2) in a patient, comprising administering a therapeutically effective amount of the pharmaceutical composition of claim 7 to said patient.

* * * * *

UNITED STATES PATENT AND TRADEMARK OFFICE
CERTIFICATE OF CORRECTION

PATENT NO. : 7,196,092 B2  Page 1 of 1
APPLICATION NO. : 11/244776
DATED : March 27, 2007
INVENTOR(S) : Timothy J. Guzi, Kamil Paruch and Michael P. Dwyer It is certified that error appears in the above-identified patent and that said Letters Patent is hereby corrected as shown below:

In the Claims:

Claim 1, col. 116, line 1:•Please delete "solvate,"
Claim 5, col. 118, line 1:•Please delete "solvate,"
Claim 6, col. 118, line 7:•Please delete "solvate,"
Claim 9, col. 118, line 51:•Please correct "kinases2" to --kinase2--

Signed and Sealed this

Twenty-ninth Day of May, 2007

JON W. DUDAS
*Director of the United States Patent and Trademark Office*